(12) United States Patent
Christofidou-Solomidou et al.

(10) Patent No.: US 10,030,040 B2
(45) Date of Patent: Jul. 24, 2018

(54) PREPARATION OF (S,S)-SECOISOLARICIRESINOL DIGLUCOSIDE AND (R,R)-SECOISOLARICIRESINOL DIGLUCOSIDE

(71) Applicants: The Trustees of the University of Pennsylvania, Philadelphia, PA (US); The Scripps Research Institute, La Jolla, CA (US)

(72) Inventors: Melpo Christofidou-Solomidou, Eagleville, PA (US); Kyriacos C. Nicolaou, La Jolla, CA (US); Roman A. Valiulin, Atlanta, GA (US); Nicholas Simmons, Houston, TX (US); Philipp M. Heretsch, Houston, TX (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 226 days.

(21) Appl. No.: 14/897,181

(22) PCT Filed: Jun. 10, 2014

(86) PCT No.: PCT/US2014/041636
§ 371 (c)(1),
(2) Date: Dec. 9, 2015

(87) PCT Pub. No.: WO2014/200964
PCT Pub. Date: Dec. 18, 2014

(65) Prior Publication Data
US 2016/0137682 A1  May 19, 2016

Related U.S. Application Data

(60) Provisional application No. 61/833,258, filed on Jun. 10, 2013.

(51) Int. Cl.
| | |
|---|---|
| *C07C 67/343* | (2006.01) |
| *C07C 67/31* | (2006.01) |
| *C07H 15/18* | (2006.01) |
| *C07H 15/203* | (2006.01) |
| *C07C 41/18* | (2006.01) |
| *C07C 67/303* | (2006.01) |

(52) U.S. Cl.
CPC ............ *C07H 15/18* (2013.01); *C07C 41/18* (2013.01); *C07C 67/303* (2013.01); *C07C 67/31* (2013.01); *C07C 67/343* (2013.01); *C07H 15/203* (2013.01)

(58) Field of Classification Search
CPC ..... C07C 41/18; C07C 67/303; C07C 67/343; C07H 15/203
USPC .......................................... 536/18.5; 568/644
See application file for complete search history.

(56) References Cited

U.S. PATENT DOCUMENTS

| 6,806,356 B2 | 10/2004 | Dobbins et al. |
| 2003/0060420 A1 | 3/2003 | Heintzman et al. |
| 2004/0030108 A1 | 2/2004 | Pihlava et al. |
| 2013/0203688 A1 | 8/2013 | Barbeau et al. |

FOREIGN PATENT DOCUMENTS

| CN | 101117641 A | 2/2008 |
| CN | 102050848 | 5/2011 |
| CN | 102558252 | 7/2012 |
| EP | 2514426 A1 | 10/2012 |

OTHER PUBLICATIONS

Schmidt et al reference, J. Carbohydrate Chem., 1985, 42(2), 141-169.*
Yen et al., "Antioxidative properties of methanolic extracts from peanut hulls", J. Am. Oil Chem. Soc. 1993, 70, 383.
Moree et al., "Secoisolariciresinol Diglucoside—A Phytoestrogen Nutraceutical of Flaxseed: Synthesis and Evaluation of Antioxidant Potency", Free Rad. Antiox. 2011, 1, 31.
Buranov et al., "Lignin in straw of herbaceous crops", Industrial Crops and Products, 2008, 28, pp. 237-259.
Mishra et al., "Synthesis and antioxidant evaluation of (S,S)- and (R,R)-secoisolariciresinol diglucosides (SDGs)", Bioorganic and Medicinal Chemistry Letters, vol. 23, issue 19, Aug. 2013, pp. 5325-5328.
Ford et al. "Biosynthetic Pathway to the Cancer Chemopreventive Secoisolariciresinol Diglucoside-Hydroxymethyl Glutaryl Ester-Linked Lignan Oligomers in Flax (*Linum u sitatissimum*) Seed" Journal of natural products. Nov. 26, 2001;64(11):1388-97.
Moree et al. "Investigation of in vitro and in vivo antioxidant potential of secoisolariciresinol diglucoside" Molecular and cellular biochemistry. Jan. 1, 2013;373(1-2):179-87.
Schmidt et al. "O-($\alpha$-D-glucopyranosyl) trichloroacetimidate as a glucosyl donor" Journal of Carbohydrate Chemistry. Jun. 1, 1985;4(2):141-69.
Supplementary European Search Report for European Application No. 14811683.3 dated Dec. 21, 2016.
Yang et al. "N-Dimethylphosphoryl-protected glucosamine trichloroacetimidate as an effective glycosylation donor" Tetrahedron letters. Jun. 25, 2007;48(26):4557-60.

\* cited by examiner

*Primary Examiner* — Ganapathy Krishnan
(74) *Attorney, Agent, or Firm* — Mark S. Cohen; Pearl Cohen; Zedek Latzer Baratz LLP

(57) ABSTRACT

The invention relates to processes for preparing (S,S)-secoisolariciresinol diglucoside and (R,R)-secoisolariciresinol diglucoside and compositions comprising the same.

39 Claims, 15 Drawing Sheets

PREPARATION OF (S,S)-SECOISOLARICIRESINOL DIGLUCOSIDE AND (R,R)-SECOISOLARICIRESINOL DIGLUCOSIDE

CROSS-REFERENCE TO RELATED APPLICATIONS

This application is a National Phase Application of PCT International Application No. PCT/US2014/041636, International Filing Date Jun. 10, 2014, claiming priority of Provisional Patent Application No. 61/833,258, filed Jun. 10, 2013, all of which are hereby incorporated by reference herein in its entirety.

GOVERNMENT INTEREST

This invention was made, in part, with government support under Grant Numbers R01 CA133470 and RC1AI081251, both awarded by the National Institutes of Health. The government has certain rights in the invention.

FIELD OF THE INVENTION

The invention relates to processes for preparing (S,S)-secoisolariciresinol diglucoside and (R,R)-secoisolariciresinol diglucoside, as well as compositions comprising the same.

BACKGROUND OF THE INVENTION

Ionizing radiation produces a wide range of deleterious effects in living organisms. Humans are exposed to radiation during diagnostic and therapeutic radiographic procedures, when using electron devices, from background radiation of nuclear accidents, and during sir and space travel. Current global developments have additionally established terrorism as dangerous means by which potentially large numbers of people can be exposed to lethal amounts of radiation. It is, therefore, of high importance to identify radioprotective agents that can be administered both before exposure to radiation, and as treatment after radioactive exposure.

Natural products and their analogs are increasingly considered as promising leads for the discovery and development of radioprotectors. Both (2R,3R)- and (2S,3S)]-enantiomers of secoisolariciresinol and meso-secoisolariciresinol have been detected in plants, but only the (2R,3R)-[(−)secoisolariciresinol]-isomer occurs abundantly. Although this compound is available by extraction from flaxseed, the necessary subsequent purification is a non-trivial and tedious process. Accordingly, there exists a need to develop a short and enantioselective synthesis to prepare enantiopure secoisolariciresinol from readily available commercial materials.

SUMMARY OF THE INVENTION

The present invention provides a process for preparing a compound of formula ((S,S)-SDG-1) ((S,S)-secoisolariciresinol diglucosides-1)

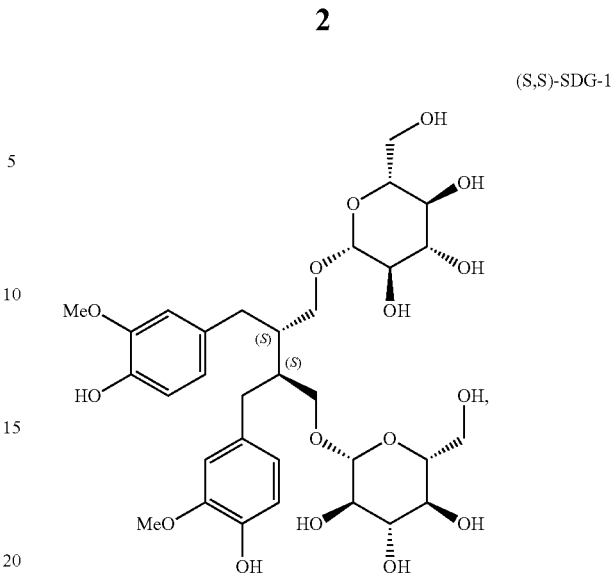

the process comprising:
a) reacting a compound of formula (6)

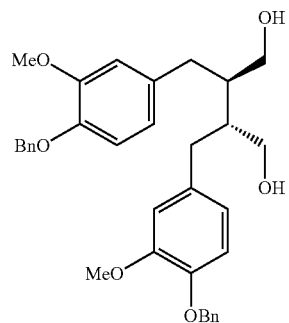

with a compound of formula (7)

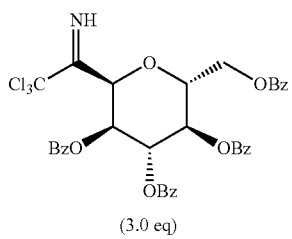

to prepare a compound of formula ((S,S)-S3)

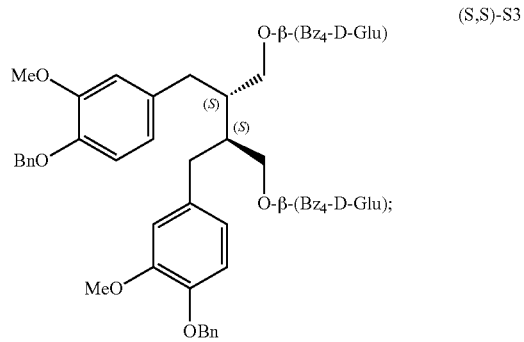

(b) cleaving benzyl ethers of the compound of formula ((S,S)-S3), followed by a separation procedure to prepare a compound of formula ((S,S)-8)

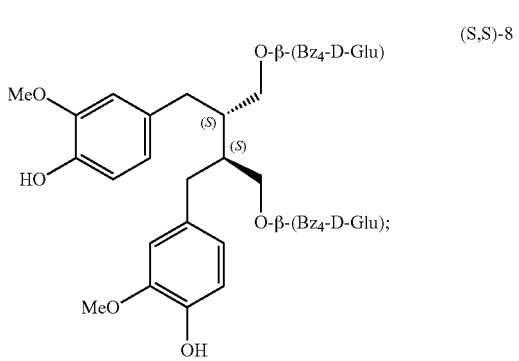

and
(c) deprotecting the compound of formula ((S,S)-8) to prepare the compound of formula ((S,S)-SDG-1).

The present invention provides a process for preparing a compound of formula ((S,S)-SDG-1)

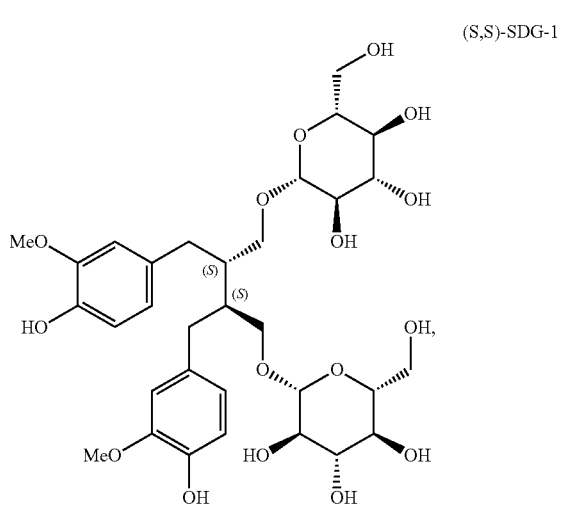

the process comprising:

(a) reacting a compound of formula (5)

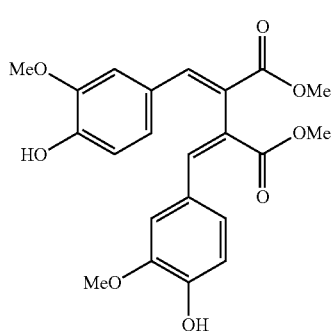

with a reducing agent to prepare a compound of formula (S1)

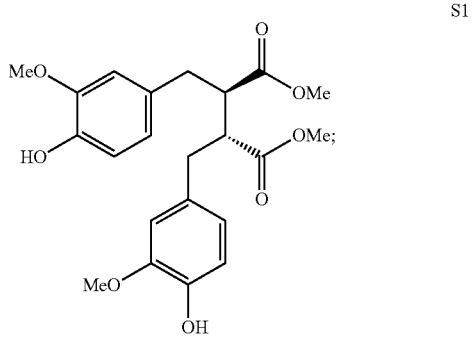

(b) reacting the compound of formula (S1) with a benzylating agent to prepare a compound of formula (S2)

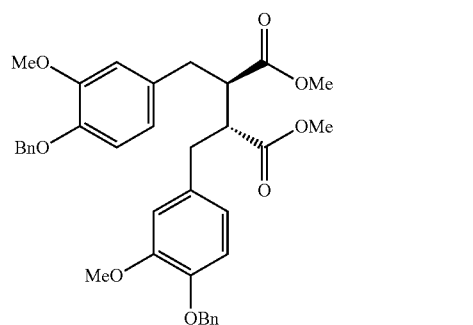

(c) reacting the compound of formula (S2) with a reducing agent to prepare a compound of formula (6);
(d) reacting the compound of formula (6) with a compound of formula (7) to prepare a compound of formula ((S,S)-S3);
(e) cleaving benzyl ethers of the compound of formula ((S,S)-S3), followed by a separation procedure to prepare a compound of formula ((S,S)-8); and
(f) deprotecting the compound of formula ((S,S)-8) to prepare the compound of formula ((S,S)-SDG-1).

The present invention further provides a process for preparing a compound of formula ((S,S)-SDG-1), the process comprising:

(a) reacting a compound of formula (S2) with a reducing agent to prepare a compound of formula (6);
(b) reacting the compound of formula (6) with a compound of formula (7) to prepare a compound of formula ((S,S)-S3);
(c) cleaving benzyl ethers of the compound of formula ((S,S)-S3), followed by a separation procedure to prepare a compound of formula ((S,S)-8); and
(d) deprotecting the compound of formula ((S,S)-8) to prepare the compound of formula ((S,S)-SDG-1).

The present invention further provides a process for preparing a compound of formula ((R,R)-SDG-2))(R,R)-secoisolariciresinol diglucosides-2)

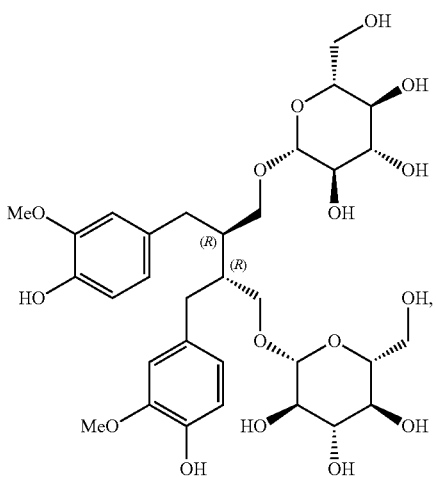

(R,R)-SDG-2 the process comprising:
b) reacting a compound of formula (6) with a compound of formula (7) to prepare a compound of formula ((R,R)-S4)

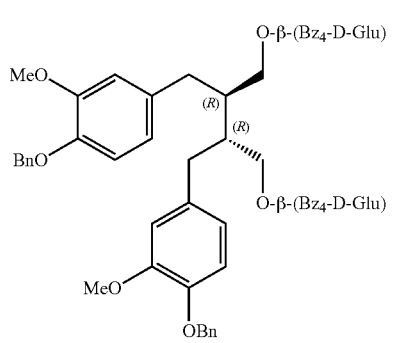

(R,R)-S4

(a) cleaving benzyl ethers of the compound of formula ((R,R)-S4), followed by a separation procedure to prepare a compound of formula ((R,R)-9)

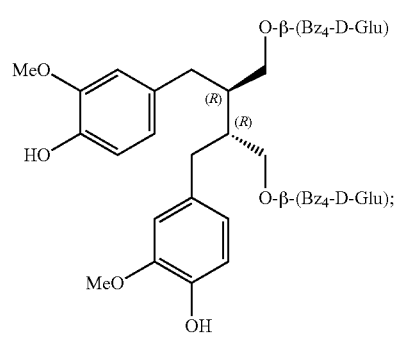

(R,R)-9 and
(c) deprotecting the compound of formula ((R,R)-9) to prepare the compound of formula ((R,R)-SDG-2).

The present invention further provides a process for preparing a compound of formula ((R,R)-SDG-2), the process comprising:
(a) reacting a compound of formula (5) with a reducing agent to prepare a compound of formula (S1);
(b) reacting the compound of formula (S1), with a benzylating agent to prepare a compound of formula (S2);
(c) reacting the compound of formula (S2) with a reducing agent to prepare a compound of formula (6);
(d) reacting the compound of formula (6) with a compound of formula (7) to prepare a compound of formula ((R,R)-S4);
(e) cleaving benzyl ethers of the compound of formula ((R,R)-S3), followed by a separation procedure to prepare a compound of formula ((R,R)-9); and
(f) deprotecting the compound of formula ((R,R)-9) to prepare the compound of formula ((R,R)-SDG-2).

The present invention further provides a process for preparing a compound of formula ((R,R)-SDG-2), the process comprising:
(a) reacting a compound of formula (S2), with a reducing agent to prepare a compound of formula (6),
(b) reacting the compound of formula (6) with a compound of formula (7) to prepare a compound of formula ((R,R)-S4);
(c) cleaving benzyl ethers of the compound of formula ((R,R)-S4), followed by a separation procedure to prepare a compound of formula ((R,R)-9); and
(d) deprotecting the compound of formula ((R,R)-9) to prepare the compound of formula ((R,R)-SDG-2).

The present invention further provides a process for preparing a compound of formula (6), the process comprising reacting a compound of formula (S2) with a reducing agent to prepare the compound of formula (6).

The present invention further provides a process for preparing a compound of formula ((S,S)-S3), the process comprising reacting a compound of formula (6) with a compound of formula (7) to prepare the compound of formula ((S,S)-S3).

The present invention further provides a process for preparing a compound of formula ((S,S)-8), the process comprising:
(a) reacting a compound of formula (6) with a compound of formula (7) to prepare a compound of formula ((S,S)-S3);
(b) cleaving benzyl ethers of the compound of formula ((S,S)-S3), followed by a separation procedure to prepare the compound of formula ((S,S)-8).

The present invention provides a process for preparing a compound of formula ((R,R)-S4), the process comprising reacting a compound of formula (6) with a compound of formula (7) to prepare a compound of formula ((R,R)-S4)

The present invention provides a process for preparing a compound of formula ((R,R)-9), the process comprising:
(a) reacting a compound of formula (6) with a compound of formula (7) to prepare a compound of formula ((R,R)-S4);
(b) cleaving benzyl ethers of the compound of formula ((R,R)-S4), followed by a separation procedure to prepare a compound of formula ((R,R)-9).

The present invention further provides a composition, such as a pharmaceutical composition, comprising a compound of formula ((S,S)-SDG-1).

The present invention further provides a composition, such as a pharmaceutical composition, comprising a compound of formula ((R,R)-SDG-2).

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

DETAILED DESCRIPTION OF THE INVENTION

Figure 1:
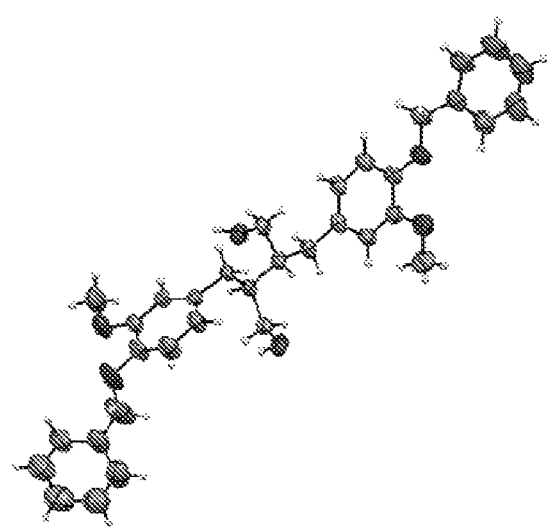
FIG. 1 depicts an ORTEP representation of dihydroxy compound 6.

The present invention provides a process for preparing a compound of formula ((S,S)-SDG-1)

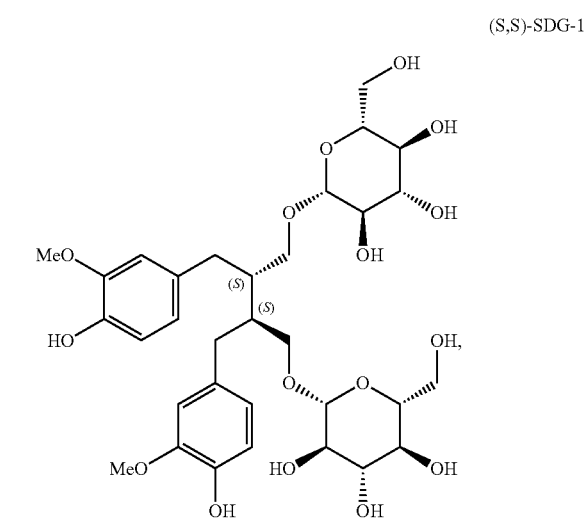

the process comprising:

(a) reacting a compound of formula (6)

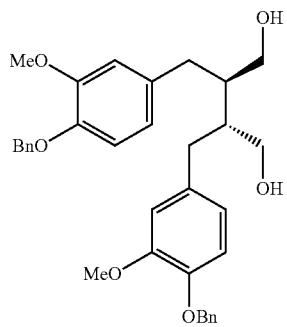

with a compound of formula (7)

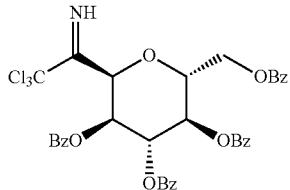

to prepare a compound of formula ((S,S)-S3)

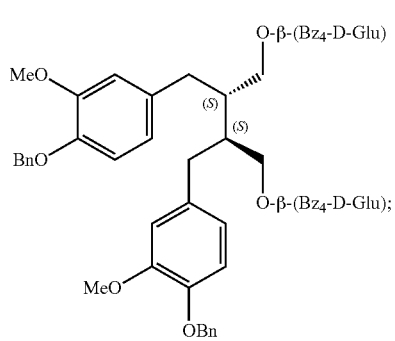

(b) cleaving benzyl ethers of the compound of formula ((S,S)-S3), followed by a separation procedure to prepare a compound of formula ((S,S)-8)

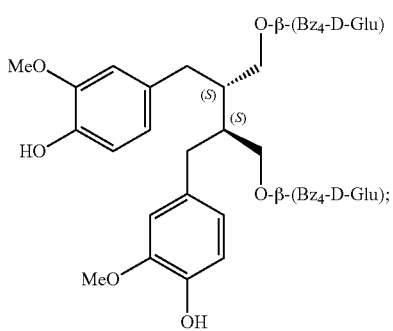

and (c) deprotecting the compound of formula ((S,S)-8) to prepare the compound of formula ((S,S)-SDG-1).

In some embodiments, said reacting is carried out in the presence of a Lewis acid. In certain embodiments, said Lewis acid is TMSOTf. In some embodiments, said reacting is carried out in the presence of activated molecular sieves.

In some embodiments, said cleaving is carried out in MeOH in the presence of $H_2$ and Pd/C.

In some embodiments, said separation procedure is carried out using preparative thin layer chromatography.

In some embodiments, said deprotecting is carried out in a solution of NaOMe and MeOH.

In some embodiments, said compound of formula (6) is prepared by the process comprising reacting a compound of formula (S2)

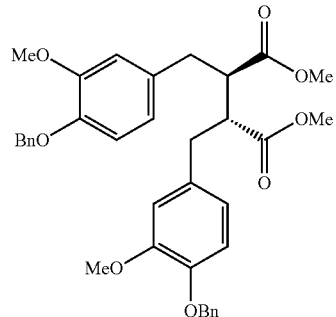

with a reducing agent to prepare the compound of formula (6). In some embodiments, said reducing agent is lithium aluminum hydride (LAH) in THF.

In some embodiments, said compound of formula (S2) is prepared by the process comprising reacting a compound of formula (S1)

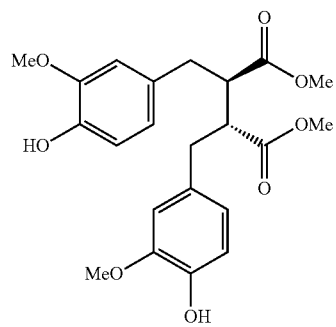

with a benzylating agent to prepare the compound of formula (S2). In some embodiments, said benzylating agent is BnBr and NaH.

In some embodiments, said compound of formula (S1) is prepared by the process comprising reacting a compound of formula (5)

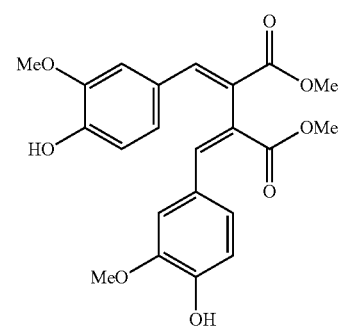

with a reducing agent to prepare the compound of formula (S1). In some embodiments, said reducing agent is $H_2$ and Pd/C.

In some embodiments, said compound of formula (5) is prepared by the process comprising reacting a compound of formula (4)

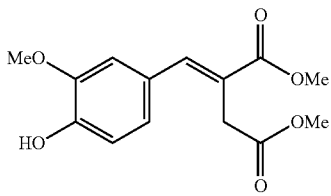

4 with vanillin by a Stobbe condensation reaction, followed by an esterification reaction to prepare the compound of formula (5). In some embodiments, said Stobbe condensation reaction is carried out in MeOH and in the presence of lithium (e.g., lithium wires). In some embodiments, said esterification reaction is carried out with MeOH in the presence of $H_2SO_4$.

In some embodiments, said compound of formula (4) is prepared by the process comprising reacting vanillin with methyl succinate via a Stobbe condensation reaction, followed by an esterification reaction. In some embodiments, said Stobbe condensation reaction is carried out in MeOH and in the presence of lithium wires. In some embodiments, said esterification reaction is carried out with MeOH in the presence of $H_2SO_4$.

The present invention provides a process for preparing a compound of formula ((S,S)-SDG-1)

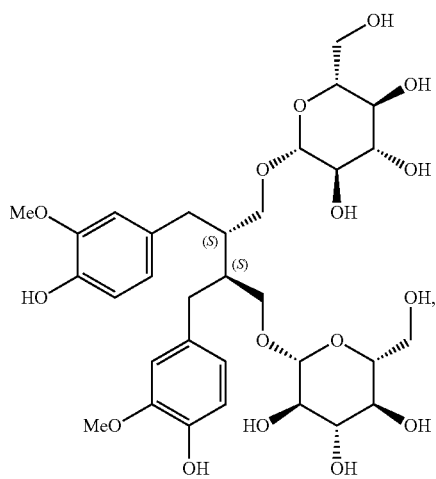

(S,S)-SDG-1 the process comprising:
(a) reacting a compound of formula (S2)

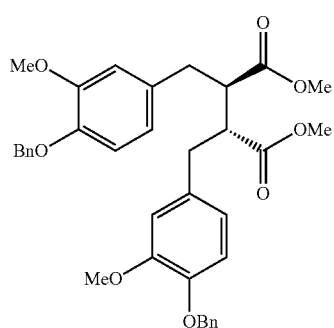

S2 with a reducing agent to prepare a compound of formula (6)

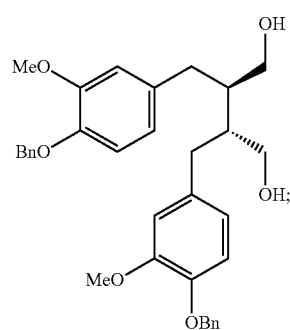

6

(b) reacting the compound of formula (6) with a compound of formula (7)

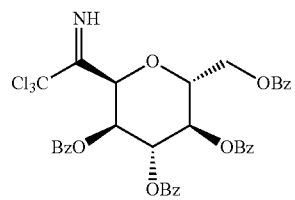

7 to prepare a compound of formula ((S,S)-S3)

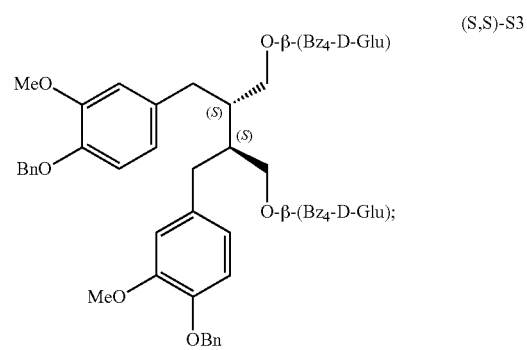

(S,S)-S3

(c) cleaving benzyl ethers of the compound of formula ((S,S)-S3), followed by a separation procedure to prepare a compound of formula ((S,S)-8)

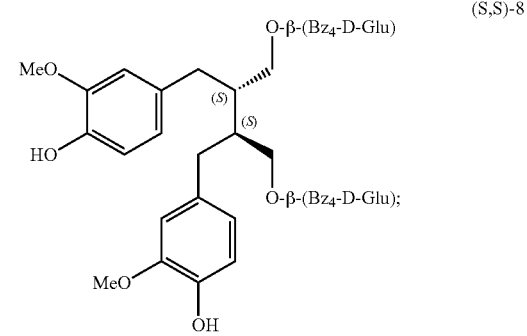

(S,S)-8 and
(d) deprotecting the compound of formula ((S,S)-8) to prepare the compound of formula ((S,S)-SDG-1).

In some embodiments, said reacting of step (a) is carried out in the presence of TMSOTf. In some embodiments, said reacting of step (a) is carried out in the presence of activated molecular sieves.

In some embodiments, said cleaving is carried out in the presence $H_2$ and Pd/C in MeOH.

In some embodiments, said separation procedure is carried out using preparative thin layer chromatography.

In some embodiments, said deprotecting is carried out in a solution of NaOMe and MeOH.

In some embodiments, said reducing agent is lithium aluminum hydride (LAH) in THF.

In some embodiments, said compound of formula (S2) is prepared by the process comprising reacting a compound of formula (S1)

S1

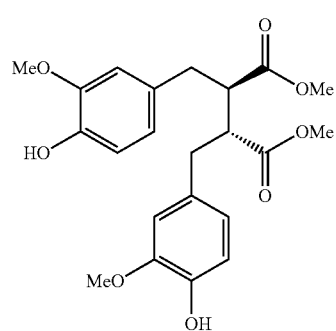

with a benzylating agent to form the compound of formula (S2). In some embodiments, said benzylating agent is BnBr and NaH.

In some embodiments, said compound of formula (S1) is prepared by the process comprising reacting a compound of formula (5)

5

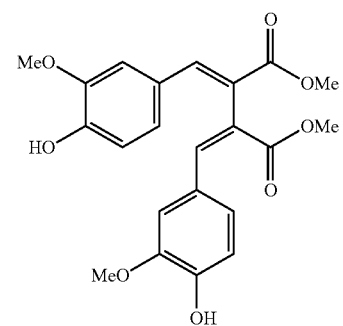

with a reducing agent to prepare the compound of formula (S1). In some embodiments, said reducing agent is $H_2$ and Pd/C.

In some embodiments, said compound of formula (5) is prepared by the process comprising reacting a compound of formula (4)

4

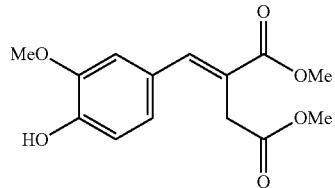

with vanillin by a Stobbe condensation reaction, followed by an esterification reaction to prepare the compound of formula (5).

In some embodiments, said Stobbe condensation reaction is carried out in MeOH and in the presence of lithium wires.

In some embodiments, In some embodiments, said esterification reaction is carried out with MeOH in the presence of $H_2SO_4$.

In some embodiments, said compound of formula (4) is prepared by the process comprising reacting vanillin with methyl succinate via a Stobbe condensation reaction, followed by an esterification reaction.

In some embodiments, said Stobbe condensation reaction is carried out in MeOH and in the presence of lithium wires. In some embodiments, said esterification reaction is carried out with MeOH in the presence of $H_2SO_4$.

The present invention provides a process for preparing a compound of formula ((S,S)-SDG-1)

(S,S)-SDG-1

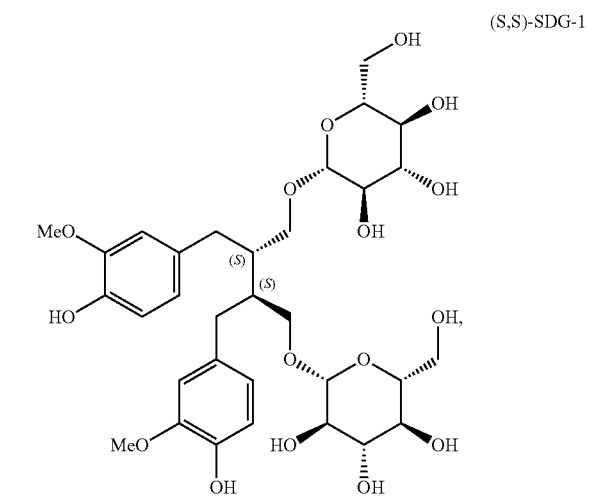

the process comprising:
(a) reacting a compound of formula (5)

5

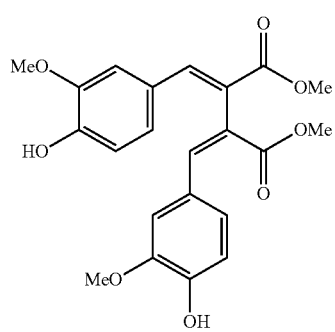

with a reducing agent to prepare a compound of formula (S1)

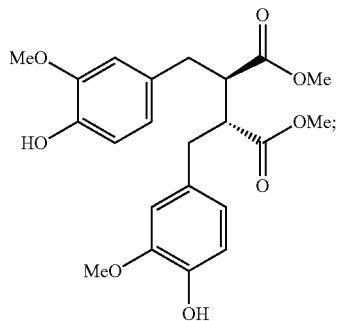

(b) reacting the compound of formula (S1)

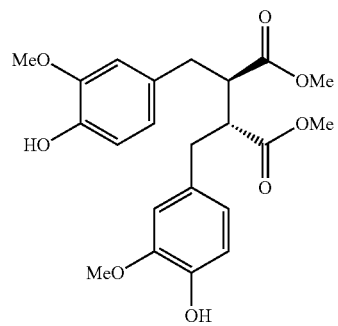

with a benzylating agent to prepare a compound of formula (S2)

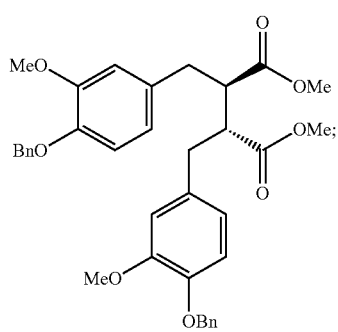

(c) reacting the compound of formula (S2) with a reducing agent to prepare a compound of formula (6)

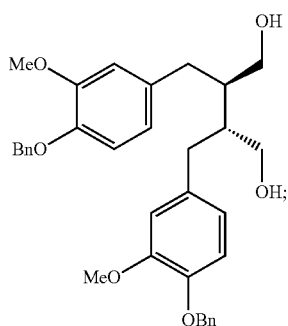

(d) reacting the compound of formula (6) with a compound of formula (7)

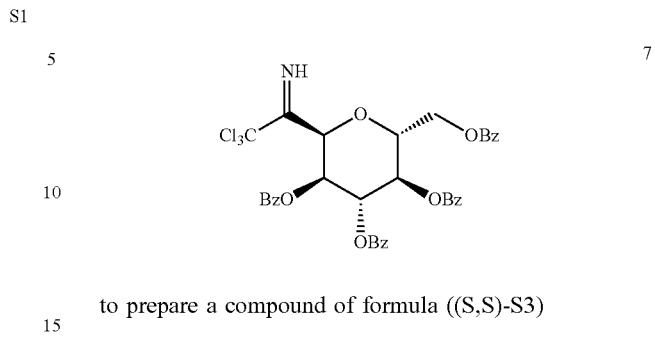

to prepare a compound of formula ((S,S)-S3)

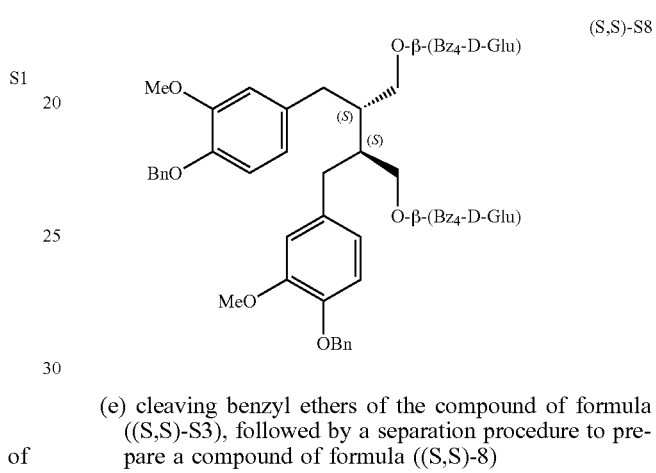

(e) cleaving benzyl ethers of the compound of formula ((S,S)-S3), followed by a separation procedure to prepare a compound of formula ((S,S)-8)

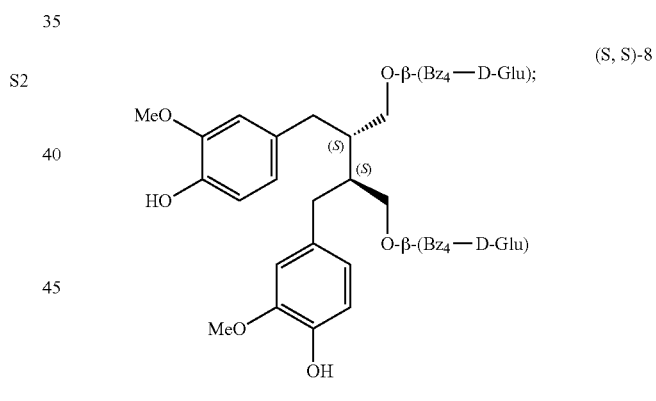

and (f) deprotecting the compound of formula ((S,S)-8) to prepare the compound of formula ((S,S)-SDG-1).

In some embodiments, In some embodiments, said compound of formula (5) is prepared by the process comprising reacting a compound of formula (4)

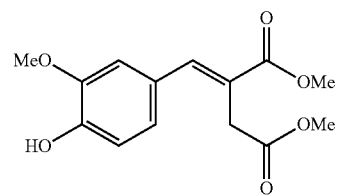

with vanillin by a Stobbe condensation reaction, followed by an esterification reaction to prepare the compound of formula (5).

The present invention provides a process for preparing a compound of formula ((R,R)-SDG-2)

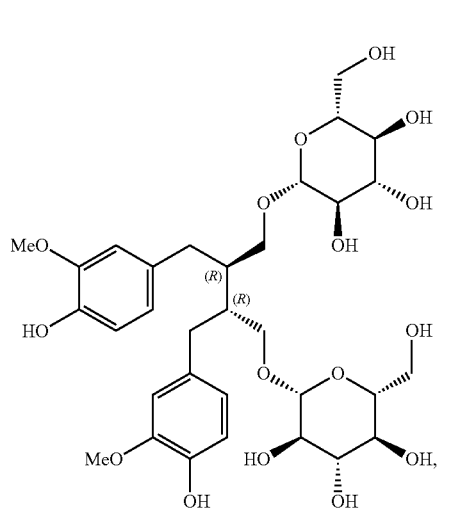

(R, R)-SDG-2 the process comprising:
(a) reacting a compound of formula (6)

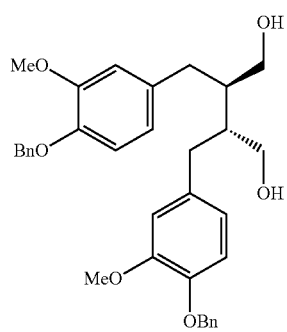

6 with a compound of formula (7)

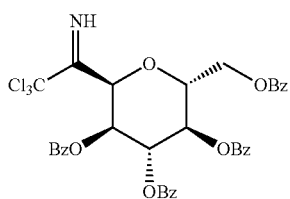

7 to prepare a compound of formula ((R,R)-S4)

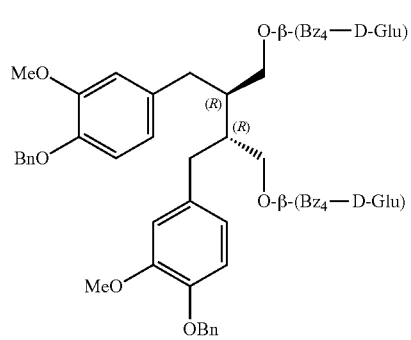

(R, R)-S4

(b) cleaving benzyl ethers of the compound of formula ((R,R)-S4), followed by a separation procedure to prepare a compound of formula ((R,R)-9)

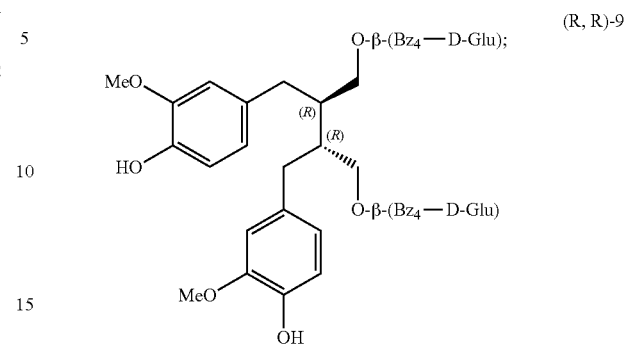

(R, R)-9 and
(c) deprotecting the compound of formula ((S,S)-9) to prepare the compound of formula ((R,R)-SDG-2).

In some embodiments, said reacting is carried out in the presence of a Lewis acid. In certain embodiments, said Lewis acid is TMSOTf.

In some embodiments, said reacting is carried out in the presence of activated molecular sieves.

In some embodiment, said cleaving is carried out in the presence of $H_2$ and Pd/C in MeOH. In some embodiments, said separation procedure is carried out using preparative thin layer chromatography.

In some embodiments, said deprotecting is carried out in a solution of NaOMe and MeOH.

In some embodiments, said compound of formula (6) is prepared by the process comprising reacting a compound of formula (S2)

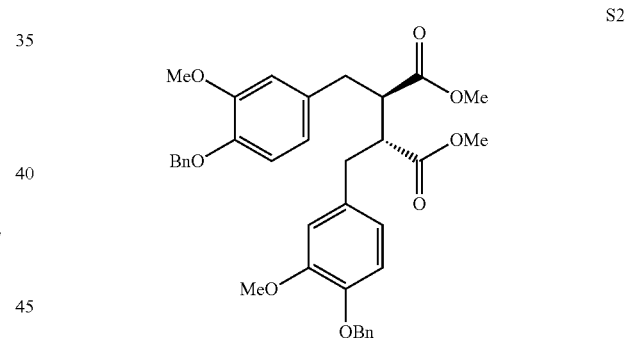

S2 with a reducing agent to prepare the compound of formula (6).

In some embodiments, said reducing agent is lithium aluminum hydride (LAH) in THF.

In some embodiments, said compound of formula (S2) is prepared by the process comprising reacting a compound of formula (S1)

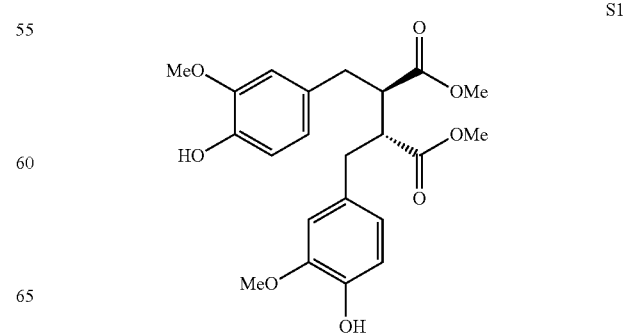

S1 with a benzylating agent to prepare the compound of formula (S2). In some embodiments, said benzylating agent is BnBr and NaH.

In some embodiments, said compound of formula (S1) is prepared by the process comprising reacting a compound of formula (5)

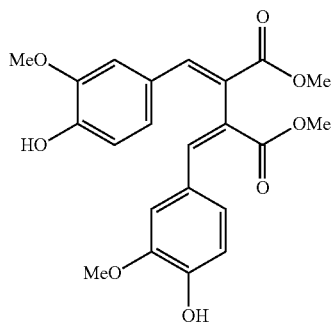

with a reducing agent to prepare the compound of formula (S1). In some embodiments, said reducing agent is $H_2$ and Pd/C.

In some embodiments, said compound of formula (5) is prepared by the process comprising reacting a compound of formula (4)

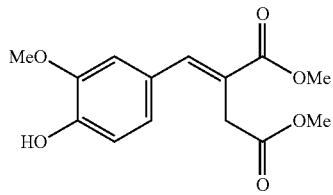

with vanillin by a Stobbe condensation reaction, followed by an esterification reaction to prepare the compound of formula (5).

In some embodiments, said Stobbe condensation reaction is carried out in MeOH and in the presence of lithium (e.g., lithium wires).

In some embodiments, said esterification reaction is carried out with MeOH in the presence of $H_2SO_4$.

In some embodiments, said compound of formula (4) is prepared by the process comprising reacting vanillin with methyl succinate via a Stobbe condensation reaction, followed by an esterification reaction.

In some embodiments, said Stobbe condensation reaction is carried out in MeOH and in the presence of lithium wires.

In some embodiments, said esterification reaction is carried out with MeOH in the presence of $H_2SO_4$.

The present invention provides a process for preparing a compound of formula ((R,R)-SDG-2)

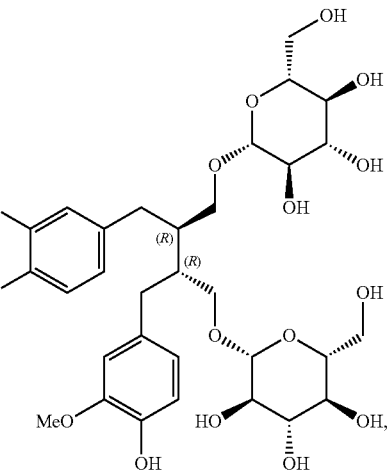

the process comprising:

(a) reacting a compound of formula (S2)

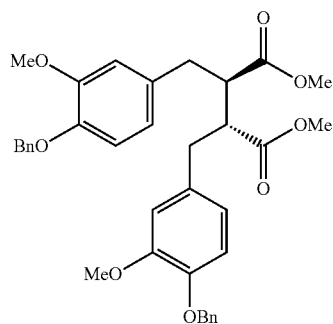

with a reducing agent to prepare a compound of formula (6)

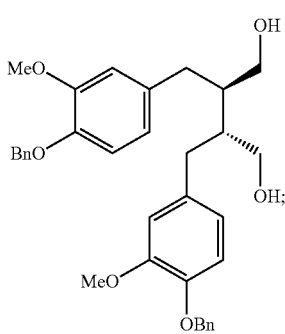

(b) reacting the compound of formula (6) with a compound of formula (7)

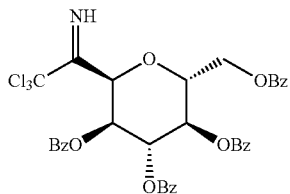

to prepare a compound of formula ((R,R)-S4)

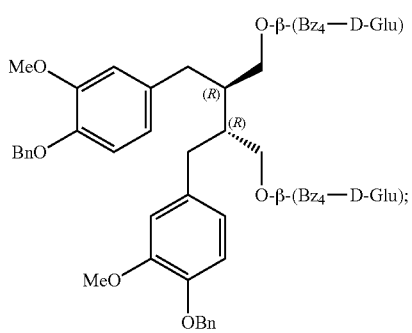

(c) cleaving benzyl ethers of the compound of formula ((R,R)-S4), followed by a separation procedure to prepare a compound of formula ((R,R)-9)

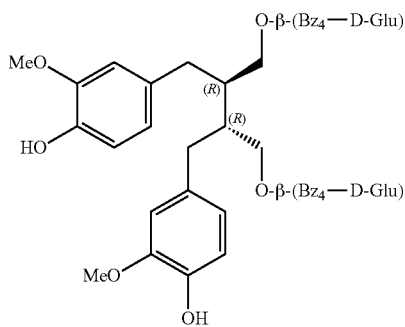

and (d) deprotecting the compound of formula ((R,R)-9) to prepare the compound of formula ((R,R)-SDG-2).

In some embodiments, said reacting of step (a) is carried out in the presence of TMSOTf. In some embodiments, said reacting of step (a) is carried out in the presence of activated molecular sieves.

In some embodiments, said cleaving is carried out in the presence $H_2$ and Pd/C in MeOH. In some embodiments, said separation procedure is carried out using preparative thin layer chromatography.

In some embodiments, said deprotecting is carried out in a solution of NaOMe and MeOH.

In some embodiments, said reducing agent is lithium aluminum hydride (LAH) in THF.

In some embodiments, said compound of formula (S2) is prepared by the process comprising reacting a compound of formula (S1)

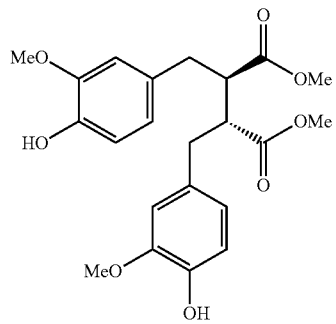

with a benzylating agent to form the compound of formula (S2).

In some embodiments, said benzylating agent is BnBr and NaH.

In some embodiments, said compound of formula (S1) is prepared by the process comprising reacting a compound of formula (5)

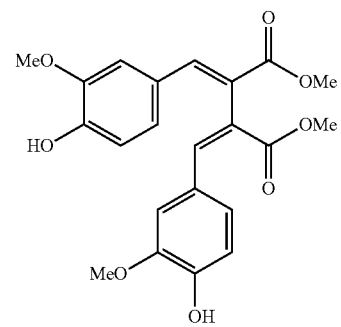

with a reducing agent to prepare the compound of formula (S1).

In some embodiments, said reducing agent is $H_2$ and Pd/C.

In some embodiments, said compound of formula (5) is prepared by the process comprising reacting a compound of formula (4)

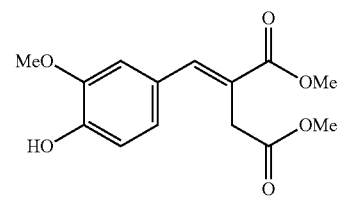

with vanillin by a Stobbe condensation reaction, followed by an esterification reaction to prepare the compound of formula (5). In some embodiments, said Stobbe condensation reaction is carried out in MeOH and in the presence of lithium wires. In some embodiments, said esterification reaction is carried out with MeOH in the presence of $H_2SO_4$.

In some embodiments, said compound of formula (4) is prepared by the process comprising reacting vanillin with methyl succinate via a Stobbe condensation reaction, followed by an esterification reaction. In some embodiments, said Stobbe condensation reaction is carried out in MeOH and in the presence of lithium wires. In some embodiments, said esterification reaction is carried out with MeOH in the presence of $H_2SO_4$.

The present invention provides a process for preparing a compound of formula ((R,R)-SDG-2)

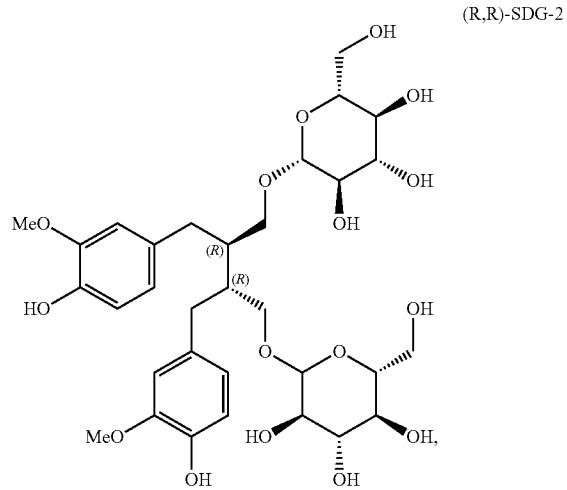

(R,R)-SDG-2 the process comprising:
(a) reacting a compound of formula (5)

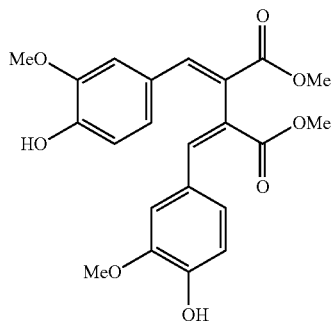

5 with a reducing agent to prepare a compound of formula (S1)

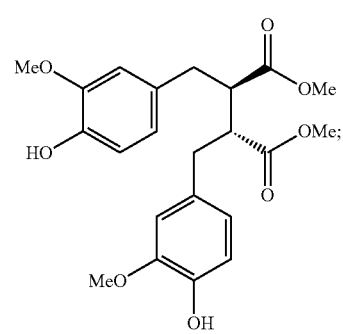

S1

(b) reacting the compound of formula (S1)

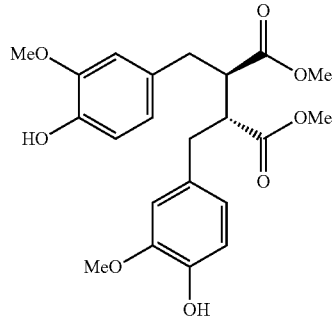

S1 with a benzylating agent to prepare a compound of formula (S2)

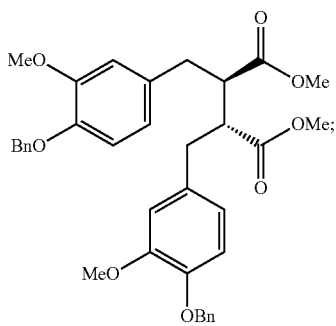

S2

(c) reacting the compound of formula (S2) with a reducing agent to prepare a compound of formula (6)

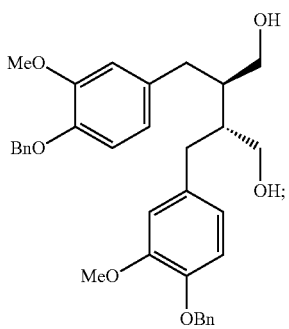

6

(d) reacting the compound of formula (6) with a compound of formula (7)

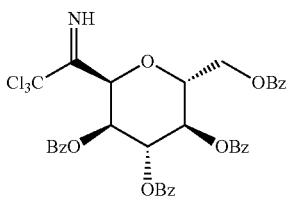

7 to prepare a compound of formula ((R,R)-S4)

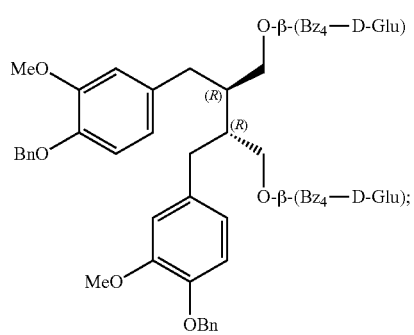

(e) cleaving benzyl ethers of the compound of formula ((R,R)-S3), followed by a separation procedure to prepare a compound of formula ((R,R)-9)

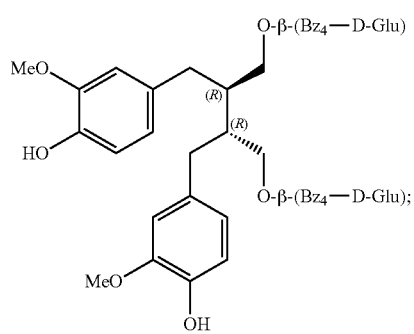

and (f) deprotecting the compound of formula ((R,R)-9) to prepare the compound of formula ((R,R)-SDG-2).

In some embodiments, said compound of formula (5) is prepared by the process comprising reacting a compound of formula (4)

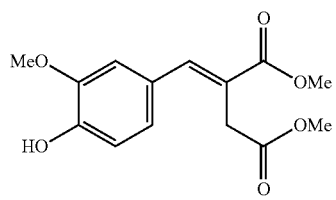

with vanillin by a Stobbe condensation reaction, followed by an esterification reaction to prepare the compound of formula (5).

The present invention provides a process for preparing a compound of formula (6)

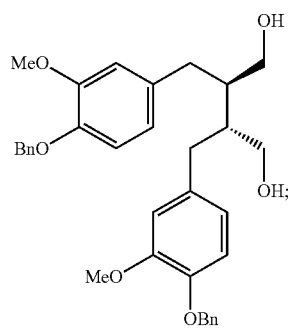

the process comprising reacting a compound of formula (S2)

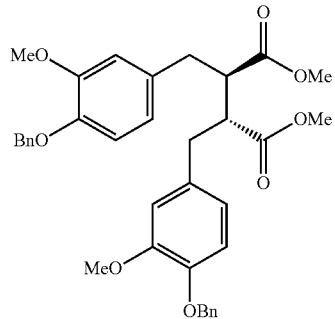

with a reducing agent to prepare the compound of formula (6). In some embodiments, said reducing agent is lithium aluminum hydride (LAH) in THF.

In some embodiments, said compound of formula (S2) is prepared by the process comprising reacting a compound of formula (S1)

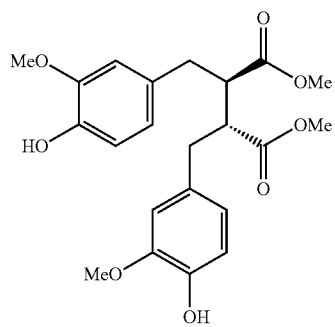

with a benzylating agent to prepare the compound of formula (S2). In certain embodimetns, said benzylating agent is BnBr and NaH.

In some embodiments, said compound of formula (S1) is prepared by the process comprising reacting a compound of formula (5)

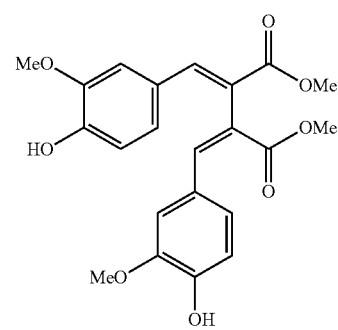

with a reducing agent to prepare the compound of formula (S1). In certain embodiments, said reducing agent is $H_2$ and Pd/C.

In some embodiments, said compound of formula (5) is prepared by the process comprising reacting a compound of formula (4)

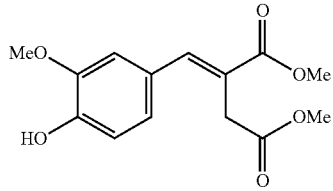
4 with vanillin by a Stobbe condensation reaction, followed by an esterification reaction to prepare the compound of formula (5). In some embodiments, said Stobbe condensation reaction is carried out in MeOH and in the presence of lithium wires. In some embodiments, said esterification reaction is carried out with MeOH in the presence of $H_2SO_4$.

In some embodiments, said compound of formula (4) is prepared by the process comprising reacting vanillin with methyl succinate via a Stobbe condensation reaction, followed by an esterification reaction. In some embodiments, said Stobbe condensation reaction is carried out in MeOH and in the presence of lithium wires. In some embodiments, said esterification reaction is carried out with MeOH in the presence of $H_2SO_4$.

The present invention provides a process for preparing a compound of formula ((S,S)-S3)

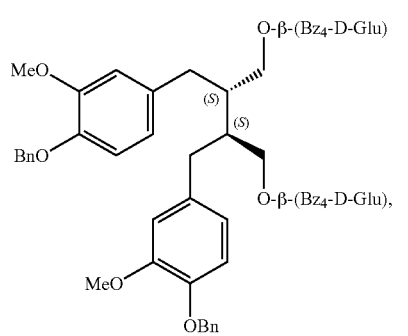
(S,S)-S3 the process comprising reacting a compound of formula (6)

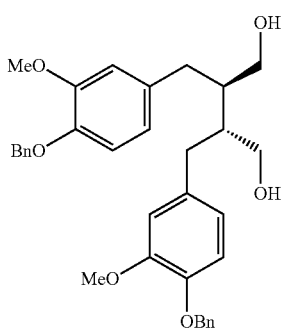
6 with a compound of formula (7)

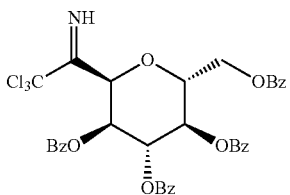
7 to prepare the compound of formula ((S,S)-S3).

In some embodiments, said reacting is carried out in the presence of a Lewis acid. In some embodiments, said Lewis acid is TMSOTf. In some embodiments, said reacting is carried out in the presence of activated molecular sieves.

In some embodiments, said compound of formula (6) is prepared by the process comprising reacting a compound of formula (S2)

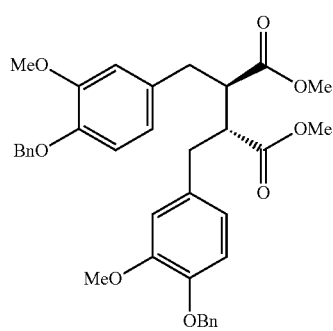
S2 with a reducing agent to prepare the compound of formula (6). In some embodiments, said reducing agent is lithium aluminum hydride (LAH) in THF.

In some embodiments, said compound of formula (S2) is prepared by the process comprising reacting a compound of formula (S1)

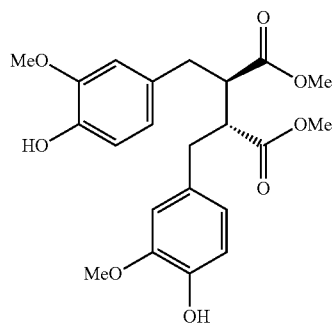
S1 with a benzylating agent to prepare the compound of formula (S2). In certain emebodiments, said benzylating agent is BnBr and NaH.

In some embodiments, said compound of formula (S1) is prepared by the process comprising reacting a compound of formula (5)

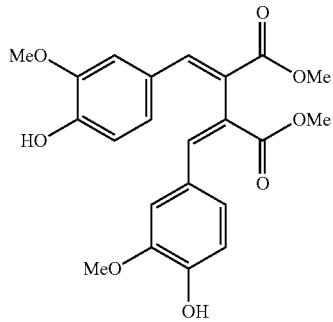

with a reducing agent to prepare the compound of formula (S1). In certain embodiments, said reducing agent is H₂ and Pd/C.

In some embodiments, said compound of formula (5) is prepared by the process comprising reacting a compound of formula (4)

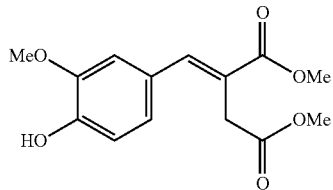

with vanillin by a Stobbe condensation reaction, followed by an esterification reaction to prepare the compound of formula (5). In some embodimetns, said Stobbe condensation reaction is carried out in MeOH and in the presence of lithium wires. In some embodiments, said esterification reaction is carried out with MeOH in the presence of H₂SO₄.

In some embodiments, said compound of formula (4) is prepared by the process comprising reacting vanillin with methyl succinate via a Stobbe condensation reaction, followed by an esterification reaction. In some embodiments, said Stobbe condensation reaction is carried out in MeOH and in the presence of lithium wires. In some embodiments, said esterification reaction is carried out with MeOH in the presence of H₂SO₄.

The present invention provides a process for preparing a compound of formula ((S,S)-8)

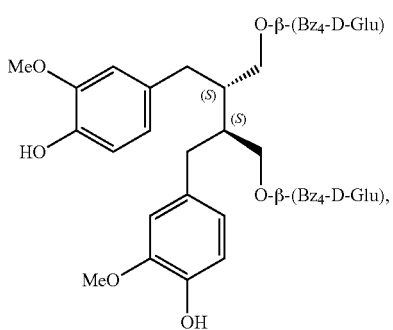

the process comprising:

(a) reacting a compound of formula (6)

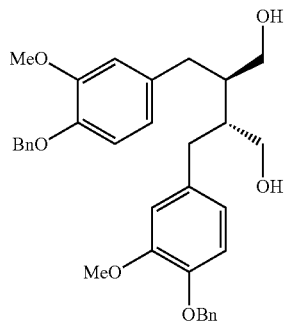

with a compound of formula (7)

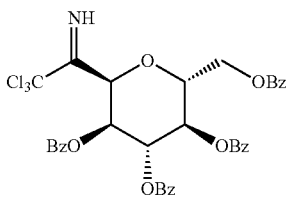

to prepare a compound of formula ((S,S)-S3)

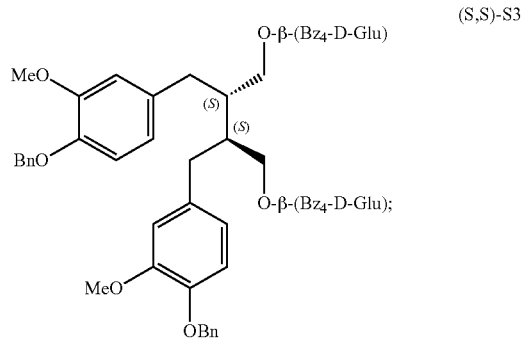

(b) cleaving benzyl ethers of the compound of formula ((S,S)-S3), followed by a separation procedure to prepare the compound of formula ((S,S)-8).

In some said reacting is carried out in the presence of TMSOTf. In some embodiments, reacting is carried out in the presence of activated molecular sieves. In some embodiments, said cleaving is carried out in the presence of H₂ and Pd/C in MeOH. In some embodiments, said separation procedure is carried out using preparative thin layer chromatography.

In some embodiments, said compound of formula (6) is prepared by the process comprising reacting a compound of formula (S2)

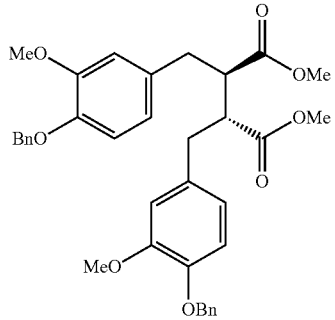

with a reducing agent to prepare the compound of formula (6). In certain embodiments, said reducing agent is lithium aluminum hydride (LAH) in THF.

In some embodiments, said compound of formula (S2) is prepared by the process comprising reacting a compound of formula (S1)

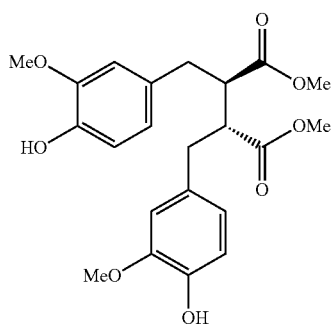

with a benzylating agent to prepare the compound of formula (S2). In certain embodiments, said benzylating agent is BnBr and NaH.

In some embodiments, said compound of formula (S1) is prepared by the process comprising reacting a compound of formula (5)

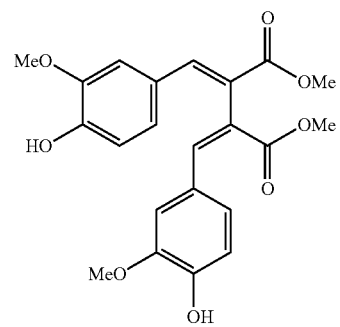

with a reducing agent to prepare the compound of formula (S1). In certain embodiments, said reducing agent is $H_2$ and Pd/C.

In some embodiments, said compound of formula (5) is prepared by the process comprising reacting a compound of formula (4)

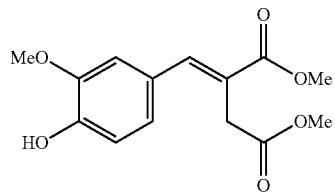

with vanillin by a Stobbe condensation reaction, followed by an esterification reaction to prepare the compound of formula (5). In some embodiments, said Stobbe condensation reaction is carried out in MeOH and in the presence of lithium wires. In some embodiemnts, said esterification reaction is carried out with MeOH in the presence of $H_2SO_4$.

In some embodiments, said compound of formula (4) is prepared by the process comprising reacting vanillin with methyl succinate via a Stobbe condensation reaction, followed by an esterification reaction. In some embodiments, said Stobbe condensation reaction is carried out in MeOH and in the presence of lithium wires. In some embodiments, said esterification reaction is carried out with MeOH in the presence of $H_2SO_4$.

The present invention provides a process for preparing a compound of formula ((R,R)-S4)

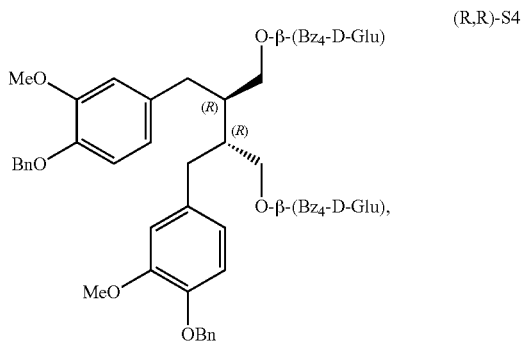

the process comprising:

(a) reacting a compound of formula (6)

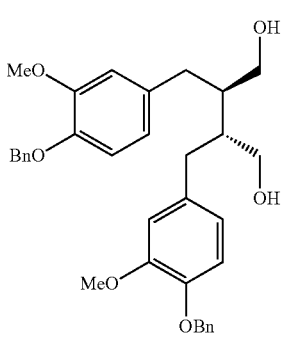

with a compound of formula (7)

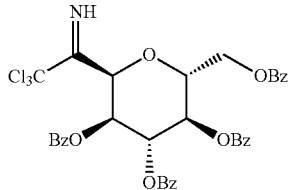

to prepare a compound of formula ((R,R)-S4).

In some embodiments, said reacting is carried out in the presence of TMSOTf.

In some embodiments, said reacting is carried out in the presence of activated molecular sieves.

In some embodiments, said compound of formula (6) is prepared by the process comprising reacting a compound of formula (S2)

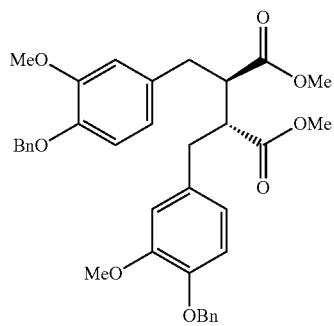

with a reducing agent to prepare the compound of formula (6). In certain embodiments, said reducing agent is lithium aluminum hydride (LAH) in THF.

In some embodiments, said compound of formula (S2) is prepared by the process comprising reacting a compound of formula (S1)

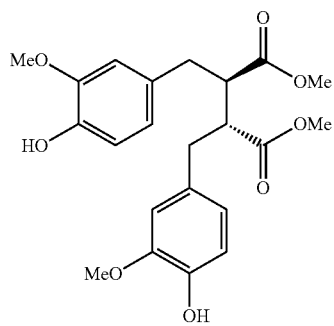

with a benzylating agent to prepare the compound of formula (S2). In certain embodiemnts, said benzylating agent is BnBr and NaH.

In some embodiments, said compound of formula (S1) is prepared by the process comprising reacting a compound of formula (5)

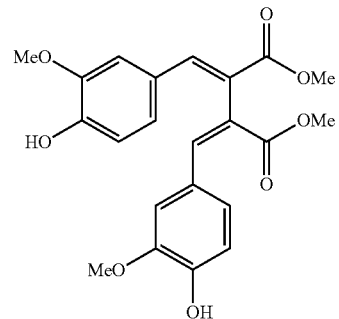

with a reducing agent to prepare the compound of formula (S1). In certain embodiemtns, said reducing agent is $H_2$ and Pd/C.

In some embodiments, said compound of formula (5) is prepared by the process comprising reacting a compound of formula (4)

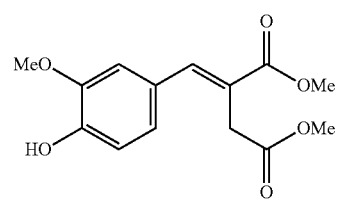

with vanillin by a Stobbe condensation reaction, followed by an esterification reaction to prepare the compound of formula (5). In some embodiments, said Stobbe condensation reaction is carried out in MeOH and in the presence of lithium wires. In some embodiments, said esterification reaction is carried out with MeOH in the presence of $H_2SO_4$.

In some embodiments, said compound of formula (4) is prepared by the process comprising reacting vanillin with methyl succinate via a Stobbe condensation reaction, followed by an esterification reaction. In some embodiments, said Stobbe condensation reaction is carried out in MeOH and in the presence of lithium wires. In some embodiments, said esterification reaction is carried out with MeOH in the presence of $H_2SO_4$.

The present invention provides a process for preparing a compound of formula ((R,R)-9)

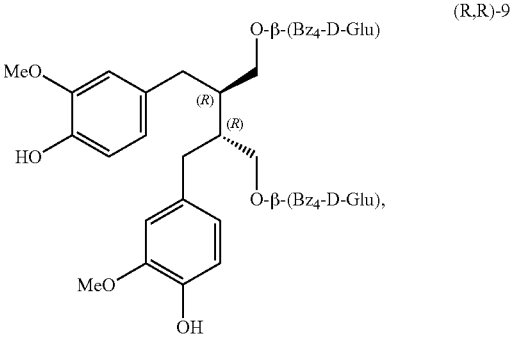

the process comprising:

(a) reacting a compound of formula (6)

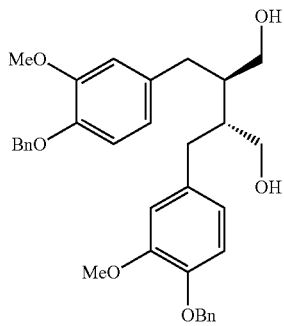

6 with a compound of formula (7)

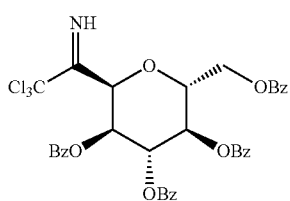

7 to prepare a compound of formula ((R,R)-S4)

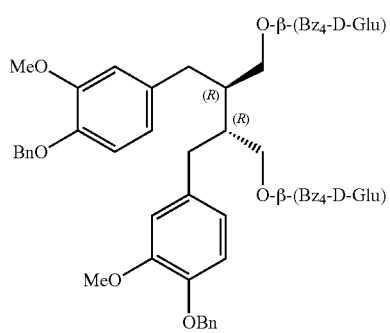

(R,R)-S4

(b) cleaving benzyl ethers of the compound of formula ((R,R)-S4), followed by a separation procedure to prepare a compound of formula ((R,R)-9).

In some embodiments, said reacting is carried out in the presence of TMSOTf. In some embodiments, said reacting is carried out in the presence of activated molecular sieves. In some embodiments, said cleaving is carried out in the presence of $H_2$ and Pd/C in MeOH. In some embodiments, said separation procedure is carried out using preparative thin layer chromatography.

In some embodiments, said compound of formula (6) is prepared by the process comprising reacting a compound of formula (S2)

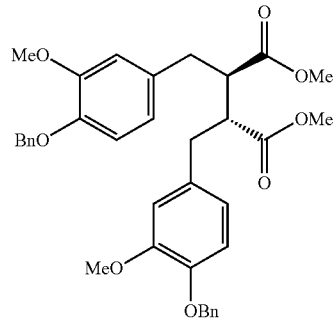

S2 with a reducing agent to prepare the compound of formula (6). In certain embodiments, said reducing agent is lithium aluminum hydride (LAH) in THF.

In some embodiments, said compound of formula (S2) is prepared by the process comprising reacting a compound of formula (S1)

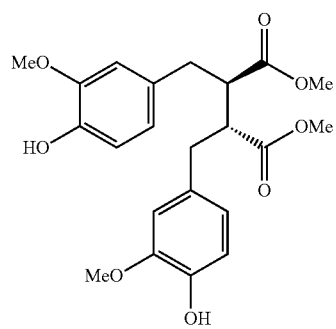

S1 with a benzylating agent to prepare the compound of formula (S2). In certain embodiments, said benzylating agent is BnBr and NaH.

In some embodiments, said compound of formula (S1) is prepared by the process comprising reacting a compound of formula (5)

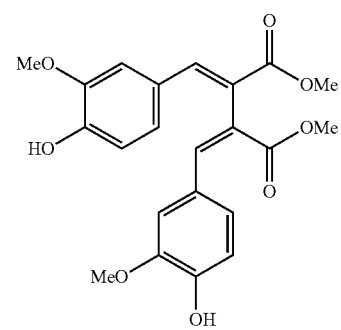

5 with a reducing agent to prepare the compound of formula (S1). In certain embodiments, said reducing agent is $H_2$ and Pd/C.

In some embodiments, said compound of formula (5) is prepared by the process comprising reacting a compound of formula (4)

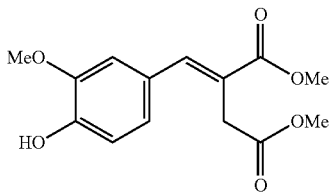

with vanillin by a Stobbe condensation reaction, followed by an esterification reaction to prepare the compound of formula (5). In some embodiments, said Stobbe condensation reaction is carried out in MeOH and in the presence of lithium wires. In some embodiments, said esterification reaction is carried out with MeOH in the presence of $H_2SO_4$.

In some embodiments, said compound of formula (4) is prepared by the process comprising reacting vanillin with methyl succinate via a Stobbe condensation reaction, followed by an esterification reaction. In some embodiments, said Stobbe condensation reaction is carried out in MeOH and in the presence of lithium wires. In some embodiments, said esterification reaction is carried out with MeOH in the presence of $H_2SO_4$.

The term "reacting" is meant to refer to the bringing together of the indicated reagents in such a way as to allow their molecular interaction and chemical transformation according to the thermodynamics and kinetics of the chemical system. Reacting can be facilitated, particularly for solid reagents, by using an appropriate solvent or mixture of solvents in which at least one of the reagents is at least partially soluble. Reacting is typically carried out for a suitable time and under conditions suitable to bring about the desired chemical transformation.

The processes described herein may include other suitable starting materials through the synthetic routes set forth above. In some embodiments, the processes described herein may also include additional steps before or after the steps described above, to add or remove suitable protecting groups. In addition, various synthetic steps may be performed in an alternate sequence or order to give the desired compounds.

In one aspect, the present invention provides a concise route for the preparation of both (S,S)-secoisolariciresinol diglucoside ((S,S)-SDG-1) and (R,R)-secoisolariciresinol diglucoside ((R,R)-SDG-2) starting from commercially available compounds, e.g., vanillin. The compounds ((S,S)-SDG-1) and ((R,R)-SDG-2) are bioactive ingredients in flaxseed. Both compounds possess strong reducing power and high free radical scavenging activity for hydroxyl, peroxyl, and DPPH (2,2-diphenyl-1-picrylhydrazyl) free readicals.

The processes of the present invention can yield substantially pure compound (S,S)-secoisolariciresinol diglucoside ((S,S)-SDG-1) and compound (R,R)-secoisolariciresinol diglucoside ((R,R)-SDG-2). For ((S,S)-SDG-1), by "substantially pure" is meant that compound ((S,S)-SDG-1) is at least substantially separated from the environment in which it was formed or detected. Substantial purity can include compositions containing at least about 80.0%, or at least about 85.0%, or at least about 90.0%, or at least about 95.0%, or at least about 97.0%, or at least about 98.0%, or at least about 99.0%, or at least about 99.2%, or at least about 99.4%, or at least about 99.6%, or at least about 99.8%, or at least about 99.9%, or even about 100% by weight of the compound. For ((R,R)-SDG-2), by "substantially pure" is meant that compound ((R,R)-SDG-2) is at least substantially separated from the environment in which it was formed or detected. Substantial purity can include compositions containing at least about 80.0%, or at least about 85.0%, or at least about 90.0%, or at least about 95.0%, or at least about 97.0%, or at least about 98.0%, or at least about 99.0%, or at least about 99.2%, or at least about 99.4%, or at least about 99.6%, or at least about 99.8%, or at least about 99.9%, or even about 100% by weight of the compound.

A "pharmaceutical composition" is a formulation containing compounds in a form suitable for administration to a subject. In some embodiments, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of a compound of the invention or a salt, solvate, polymorph, or prodrug thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of the invention include powders, sprays, ointments, pastes, creams, lotions, gels, solutions, patches and inhalants. In some embodiments, the active compound is mixed under sterile conditions with a pharmaceutically acceptable carrier, and with any preservatives, buffers, or propellants that are required.

A "subject" includes mammals, e.g., humans, companion animals (e.g., dogs, cats, birds, and the like), farm animals (e.g., cows, sheep, pigs, horses, fowl, and the like) and laboratory animals (e.g., rats, mice, guinea pigs, birds, and the like). In some embodiments, the subject is human.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used herein includes both one and more than one such excipient.

Embodiments of the invention also include compositions comprising (S,S)-secoisolariciresinol diglucoside ((S,S)-SDG-1). Preferably, these compositions are pharmaceutical compositions comprising (S,S)-secoisolariciresinol diglucoside ((S,S)-SDG-1) and at least one pharmaceutically acceptable excipient. In some embodiments, the compositions and pharmaceutical compositions may be prepared with substantially pure (S,S)-secoisolariciresinol diglucoside ((S,S)-SDG-1). In some embodiments, the compositions and pharmaceutical compositions have a diasteriomeric excess (DE) of at least 90% DE, preferably at least 95% DE, more preferably at least 98% DE, and even more preferably at least 99% DE and most preferably about 100% DE. The compositions and pharmaceutical compositions may also be prepared as mixture of the diasteriomeric forms of the compounds (e.g., as a racemic mixture or as a mixture with a ratio of 60:40, 70:30, 80:20 or 90:10 of ((S,S)-SDG-1) relative to ((R,R)-SDG-2)).

Embodiments of the invention also include compositions comprising (R,R)-secoisolariciresinol diglucoside ((R,R)-SDG-2). Preferably, these compositions are pharmaceutical compositions comprising (R,R)-secoisolariciresinol diglucoside ((R,R)-SDG-2) and at least one pharmaceutically acceptable excipient. In some embodiments, the compositions and pharmaceutical compositions may be prepared with substantially pure (R,R)-secoisolariciresinol diglucoside ((R,R)-SDG-2). In some embodiments, the compositions and pharmaceutical compositions have a diasteriomeric excess (DE) of at least 90% DE, preferably at least 95% DE, more preferably at least 98% DE, and even more preferably at least 99% DE and most preferably about 100% DE. The compositions and pharmaceutical compositions may also be prepared as mixture of the diasteriomeric forms of the compounds (e.g., as a racemic mixture or as a mixture with a ratio of 60:40, 70:30, 80:20 or 90:10 of ((R,R)-SDG-2) relative to ((S,S)-SDG-1)).

Throughout the description, where compositions are described as having, including, or comprising specific components, it is contemplated that compositions also consist essentially of, or consist of, the recited components. Similarly, where processes are described as having, including, or comprising specific process steps, the processes also consist essentially of, or consist of, the recited processing steps. Further, it should be understood that the order of steps or order for performing certain actions are immaterial so long as the invention remains operable. Moreover, two or more steps or actions may be conducted simultaneously.

The following examples are presented in order to more fully illustrate the preferred embodiments of the invention. They should in no way be construed, however, as limiting the broad scope of the invention.

EXAMPLES

General Procedures for Chemical Reactions

All reactions were carried out under an argon atmosphere with dry solvents under anhydrous conditions, unless otherwise noted. Dry tetrahydrofuran (THF), dimethylformamide (DMF), and methylene chloride ($CH_2Cl_2$) were obtained by passing commercially available pre-dried, oxygen-free formulations through activated alumina columns Yields refer to chromatographically and spectroscopically ($^1$H NMR) homogeneous materials, unless otherwise stated. Reagents were purchased at the highest commercial quality and used without further purification, unless otherwise stated. Reactions were monitored by thin-layer chromatography (TLC) carried out on 0.25 mm E. Merck silica gel plates (60F-254) using UV light as visualizing agent and an ethanolic solution of phosphomolybdic acid and cerium sulfate, and heat as developing agents. E. Merck silica gel (60, particle size 0.040-0.063 mm) was used for flash column chromatography. Preparative thin-layer chromatography (PTLC) separations were carried out on 0.25 or 0.50 mm E. Merck silica gel plates (60F-254) unless otherwise noted. NMR spectra were recorded on a Bruker DRX-600 instrument and calibrated using residual undeuterated solvent as an internal reference. The following abbreviations were used to explain the multiplicities: s=singlet, d=doublet, t=triplet, m=multiplet. IR spectra were recorded on a Perkin-Elmer Spectrum 100 FT-IR spectrometer. High-resolution mass spectra (HR-MS) were recorded on a VG ZAB-ZSE mass spectrometer using ESI (electrospray ionization).

Scheme 1 shows a reaction route that was used in the synthesis of compound (6), an intermediate compound for the preparation of (S,S)-secoisolariciresinol diglucosides and (R,R)-secoisolariciresinol diglucosides.

Scheme 1: Synthesis of compound (6)

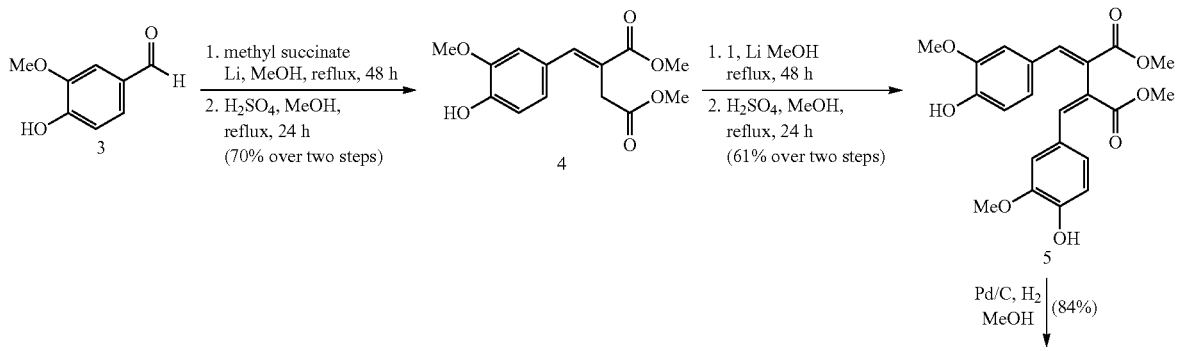

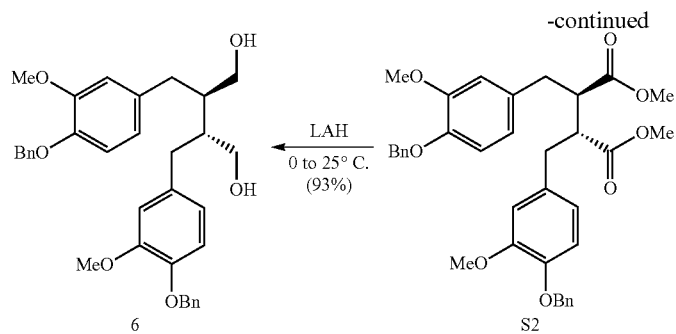
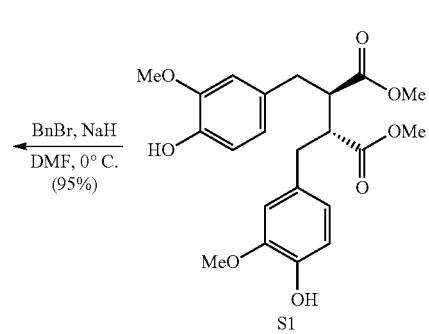

Example 1: Synthesis of Phenol 4

Example 2: Synthesis of Diester 5

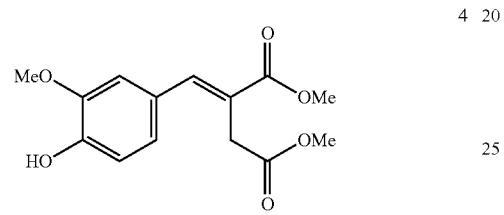

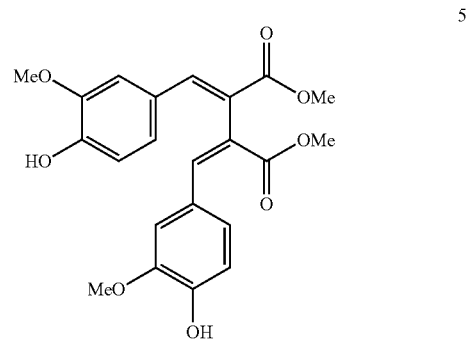 [SMILES: COC(=O)C(=C\c1ccc(O)c(OC)c1)/C(=C\c1ccc(O)c(OC)c1)C(=O)OC]

To a solution of vanillin 3 (14.0 g, 92.1 mmol, 1 equiv) and dimethyl succinate (12.13 mL, 92.1 mmol, 1 equiv) in MeOH (450 mL), lithium wire (1.79 g, 257.9 mmol, 2.8 equiv) was added slowly piecewise with an ice bath to control the exotherm. After the initial lithium had fully dissolved, more lithium (1.98 g, 285.5 mmol, 3.1 equiv) was added slowly piecewise and stirred until fully dissolved. The reaction mixture was then heated at reflux for 48 h. After cooling the solution to room temperature, most of the methanol was removed by concentration on rotavap. EtOAc (1000 mL) was added and the solution was washed with a 2 M aq. HCl solution (700 mL), $H_2O$ (3×1000 mL), then brine (200 mL). The organics layer was then dried ($MgSO_4$), filtered and concentrated. The crude was dissolved in MeOH (230 ml), $H_2SO_4$ (1 mL) was added, and the solution was heated at reflux overnight. Upon cooling the next morning, $NaHCO_3$ (3.0 g) was added to quench $H_2SO_4$ and the solution was mostly concentrated by rotavap. EtOAc (500 ml) was added and the solution was washed with $H_2O$ (2×200 mL), then brine (100 mL). The organics layer was then dried ($MgSO_4$), filtered and concentrated to a brown oil. Dissolution in a small amount of $CH_2Cl_2$ and then flash column chromatography (silica, 1:9→2:8→3:7→4:6→5:5 ether:hexane) provided 4 (18.0 g, 64.2 mmol, 70% yield, unassigned olefin geometry) as an off-white solid. 4: $R_f$=0.17 (silica, ether:hexanes 1:1); IR (film): $v_{max}$=3422, 1702, 1514, 1434, 1258, 1195 1159, 1093, 1030, 924, 821 770, 729 $cm^{-1}$; $^1$H NMR (600 MHz, $CDCl_3$) δ=7.79 (s, 1H), 6.90-6.85 (m, 3H), 6.19 (s, 1H), 3.82 (s, 3H), 3.78 (s, 3H), 3.69 (s, 3H), 3.57 (s, 2H) ppm; $^{13}$C NMR (150 MHz, $CDCl_3$) δ=171.94, 168.13, 146.80, 146.61, 142.38, 126.96, 123.39, 123.31, 114.76, 111.80, 55.85, 52.24, 52.20, 33.61 ppm; HRMS (ESI-TOF): calcd for $C_{14}H_{16}O_6$ [M+H$^+$]: 280.102, found 281.1022.

To a solution of diester 4 (15.00 g, 53.52 mmol, 1 equiv) and vanillin3 (8.14 g, 53.52 mmol, 1 equiv) in MeOH (200 mL), lithium wire (2.6 g, 374.6 mmol, 7 equiv) was added slowly piecewise with an ice bath to control the exotherm and stirred until fully dissolved. The reaction mixture was then heated at reflux for 48 h. After cooling the solution to room temperature, most of the methanol was removed by concentration on rotavap. EtOAc (200 mL) was added, the solution was acidified with 2 M aq. HCl solution (500 mL), and then extracted with EtOAc (2×200 mL). The combined organics were washed with $H_2O$ (2×200 mL), then brine (200 mL), and dried ($MgSO_4$), filtered and concentrated. The residue was dissolved in MeOH (300 mL), conc. $H_2SO_4$ (1 mL) was added, and the solution was heated at reflux overnight. Upon cooling the next morning, $NaHCO_3$ (3.0 g) was added to quench $H_2SO_4$ and the solution was mostly concentrated by rotavap. EtOAc (400 ml) was added and the solution was washed with $H_2O$ (2×200 mL), then brine (100 mL). The organics layer was then dried ($MgSO_4$), filtered and concentrated. Dissolution in a small amount of $CH_2Cl_2$ and then flash column chromatography (silica, 2:1:7→3:1: 6→4:1:5 EtOAc:$CH_2Cl_2$:hexanes) provided 5 (13.6 g, 32.8 mmol, 61% yield, unassigned olefin geometry) as a yellow-orange solid. 5: $R_f$=0.28 (silica, EtOAc:hexanes 1:1); IR (film): $v_{max}$=3388, 1696, 1588, 1509, 1431, 1209, 1157, 1029, 817, 733 $cm^{-1}$; $^1$H NMR (600 MHz, $CDCl_3$) δ=7.86 (s, 2H), 7.11 (d, J=1.64 Hz, 2H), 7.04 (dd, J=8.48, 1.72 Hz, 2H), 6.82 (d, J=8.38 Hz, 2H), 6.08 (s, 2H), 3.7 (s, 6H), 3.69 (s, 6H) ppm; $^{13}$C NMR (150 MHz, $CDCl_3$) δ=168.00, 147.59, 146.54, 142.64, 127.10, 125.38, 124.06, 114.71, 111.52, 55.77, 52.51 ppm; HRMS (ESI-TOF): calcd for $C_{22}H_{22}O_8$ [M+H$^+$]: 415.1387, found 415.1378.

Example 3: Synthesis of Diester S1

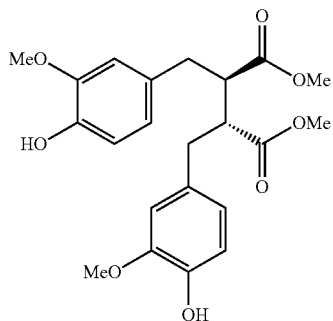

A solution of 5 (5.00 g, 12.07 mmol, 1 equiv) in MeOH (120 mL) was saturated with an argon atmosphere by briefly exposing to vacuum and backfilling with argon several times. Palladium on carbon (10% Pd by weight, 0.500 g) was added and the solution was saturated with $H_2$ atmosphere by vacuum/backfill $H_2$. The solution was stirred overnight. The next morning the solution was put under an argon atmosphere, $CH_2Cl_2$ (400 mL) was added, and the solution was allowed to stir for 1 h. The mixture was then filtered through a pad of Celite (1.5 in, washing with MeOH and $CH_2Cl_2$), and the filtrate was concentrated. The resulting solid was dissolved in a small amount of $CH_2Cl_2$ and purified by flash column chromatography (2:8:1→3:7:1→4:6:1 EtOAc:hexanes:$CH_2Cl_2$) to give 51 (4.24 g, 10.1 mmol, 84%) as an off-white solid. S1: $R_f$=0.24 (silica, EtOAc:hexanes:$CH_2Cl_2$ 4:6:1); IR (film): $v_{max}$=3440, 2951, 1726, 1514, 1432, 1267, 1198, 1151, 1121, 1029, 817, 797 cm$^{-1}$; $^1$H NMR (600 MHz, CDCl$_3$) δ=6.78 (d, J=8.09 Hz, 2H), 6.58 (d, J=8.09 Hz, 2H), 6.45 (s, 2H), 5.65 (s, 2H), 3.75 (s, 6H), 3.64 (s, 6H), 3.00-2.94 (m, 2H), 2.92-2.82 (m, 4H) ppm; $^{13}$C NMR (150 MHz, CDCl$_3$) δ=174.03, 146.49, 144.21, 130.41, 121.88, 114.18, 111.26, 55.73, 51.86, 47.67, 35.38 ppm; HRMS (ESI-TOF): calcd for $C_{22}H_{26}O_8$ [M+H$^+$]: 419.17, found 419.1700.

Example 4: Synthesis of Benzyl Ether S2

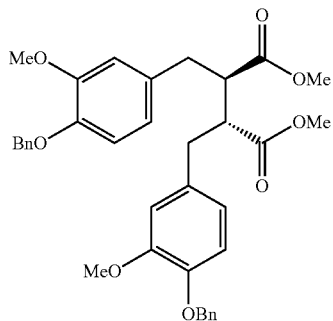

To a solution of S1 (1.00 g, 2.39 mmol, 1 equiv) in DMF (24 mL) cooled to 0° C. with an ice bath, NaH (0.201 g, 5.02 mmol, 60% dispersion, 2.1 equiv) was added slowly and the solution was stirred at 0° C. for 1 h. BnBr (910 μL, 7.65 mmol, 3.2 equiv) was added over 1 min, and the solution was stirred at 0° C. for 4 h. The reaction mixture was then poured into $H_2O$ (300 mL) and EtOAc (100 mL). The organic layer was washed with $H_2O$ (3×200 mL) and brine (1×50 mL), dried (MgSO$_4$), filtered and concentrated. The resulting solid was dissolved in a small amount of $CH_2Cl_2$ and purified by flash column chromatography (silica, 9:1:1→8:2:1 hexanes:EtOAc:$CH_2Cl_2$) to give S2 (1.36 g, 2.27, 95% yield) as a white solid. S2: $R_f$=0.23 (silica, EtOAc:hexanes 3:7); IR (film): $v_{max}$=2949, 1730, 1512, 1453, 1253, 1225, 1138, 1023, 733 cm$^{-1}$; $^1$H NMR (600 MHz, CDCl$_3$) δ=7.45-7.40 (m, 4H), 7.38-7.33 (m, 4H), 7.31-7.27 (m, 2H), 6.74 (d, J=8.12 Hz, 2H), 6.59 (d, J=1.69 Hz, 2H), 6.53 (dd, J=8.12, 1.69 Hz, 2H), 5.12 (s, 4H), 3.80 (s, 6H), 3.61 (s, 6H), 3.03-2.85 (m, 6H) ppm; $^{13}$C NMR (150 MHz, CDCl$_3$) δ=174.00, 149.58, 146.87, 137.37, 131.74, 128.65, 127.93, 127.37, 121.09, 114.05, 112.73, 71.14, 56.00, 51.91, 47.91, 35.32 ppm; HRMS (ESI-TOF): calcd for $C_{36}H_{38}O_8$ [M+H$^+$]: 599.2639, found 599.2651.

Example 5: Synthesis of Diol 6

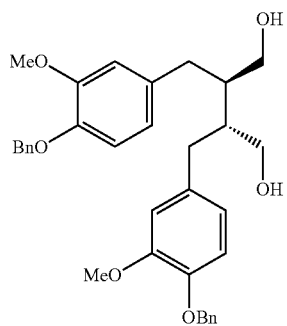

To a solution of S2 (0.341 g, 0.570 mmol, 1 equiv) in THF (6 mL) at 0° C., lithium aluminum hydride (1 M soln in THF, 1.14 mL, 1.14 mmol, 2 equiv) was added dropwise. The solution was allowed to come to 25° C. overnight. The resulting mixture was poured into a flask containing $H_2O$ (200 mL) and EtOAc (100 mL). Then 50 mL of an aq. sat. soln of Rochelle's salt was added and the mixture was stirred until the layers were readily separable. The organic layer was then washed with $H_2O$ (2×100 mL) and brine (1×50 mL), and dried (MgSO$_4$), filtered and concentrated. The resulting solid was dissolved in a small amount of $CH_2Cl_2$ and purified by flash column chromatography (silica, 5:5:1→7:3:1→8:2:1 EtOAc:hexanes:$CH_2Cl_2$) to give diol 6 (0.286 g, 0.527 mmol, 93% yield) as a white solid. 6: $R_f$=0.2 (silica, 6:4 EtOAc:hexanes); IR (film): $v_{max}$=3287, 2933, 1510, 1453, 1259, 1223, 1137, 1009, 733, 695 cm$^{-1}$; $^1$H NMR (600 MHz, CDCl$_3$) δ=7.47-7.42 (m, 4H), 7.40-7.34 (m, 4H), 7.33-7.28 (m, 2H), 6.78 (d, J=8.15 Hz, 2H), 6.69 (s, 2H), 6.62 (d, J=8.15 Hz, 2H), 5.11 (s, 4H), 4.09 (s, 2H), 3.82 (s, 6H), 3.78 (d, J=11.07 Hz, 2H), 3.49 (d, J=11.07 Hz, 2H), 2.80-2.72 (m, 2H), 2.69-2.62 (m, 2H), 1.86 (s, 2H) ppm; $^{13}$C NMR (150 MHz, CDCl$_3$) δ 149.47, 146.38, 137.29, 133.87, 128.51, 127.80, 127.28, 121.02, 114.02, 112.79, 71.12, 60.19, 55.96, 43.79, 35.81 ppm; HRMS (ESI-TOF): calcd for $C_{34}H_{38}O_6$ [M+H$^+$]: 543.2741, found 543.2741.

Scheme 2 shows a reaction route that was used in the synthesis of (S,S)-secoisolariciresinol diglucosides and (R,R)-secoisolariciresinol diglucosides, starting from compound (6).

Scheme 2: Synthesis of ((S,S)-SDG-1) and ((R,R)-SDG-2) from compound (6)
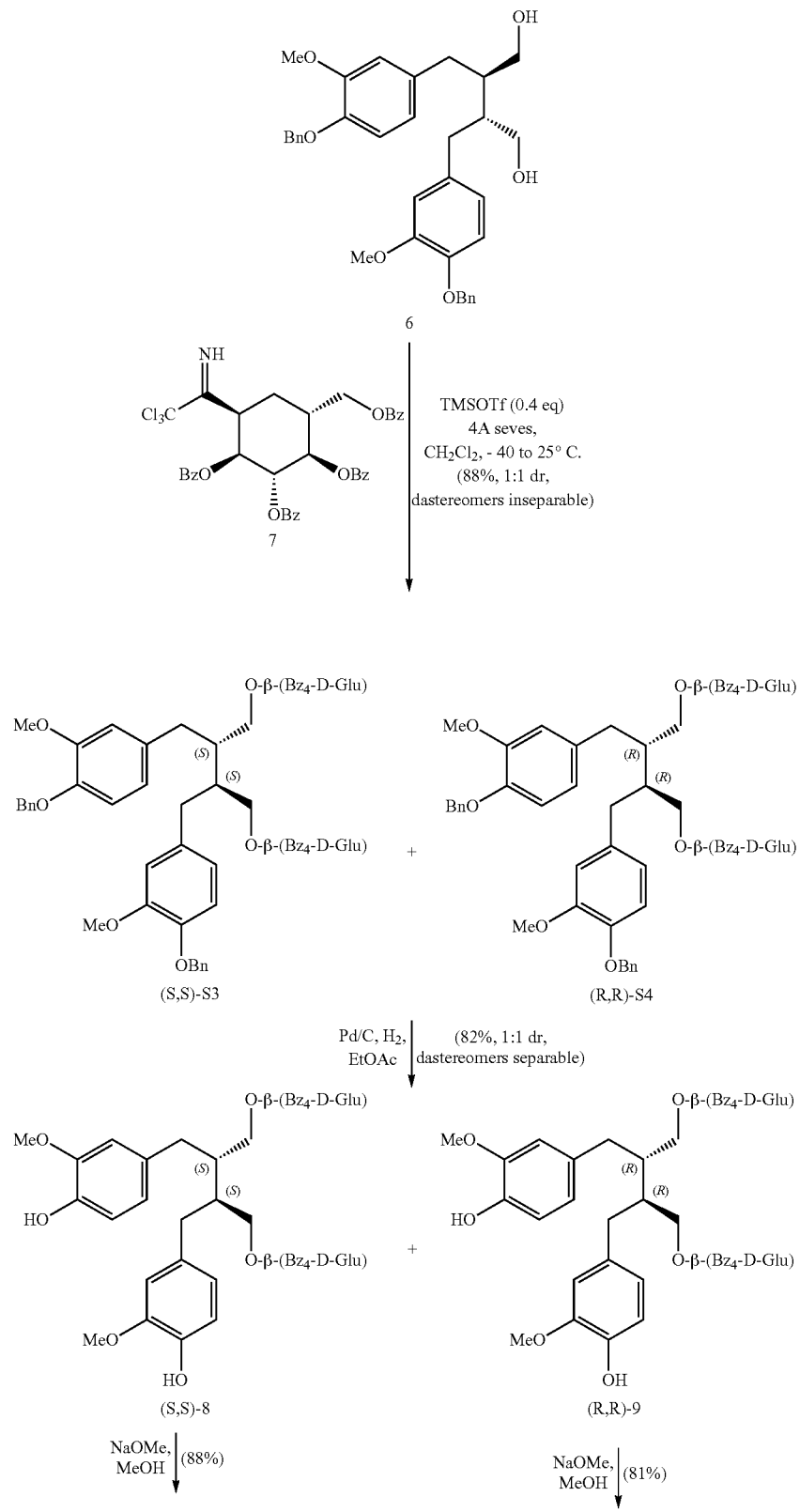

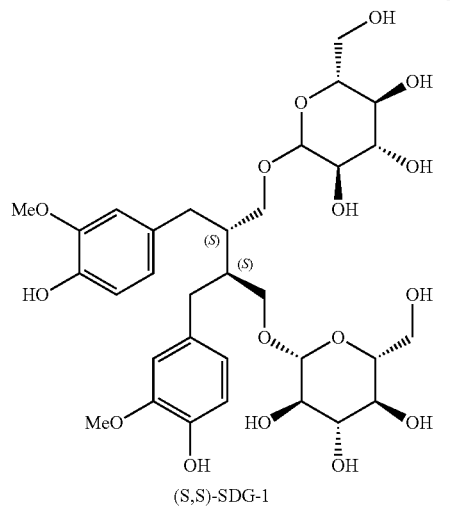

(S,S)-SDG-1

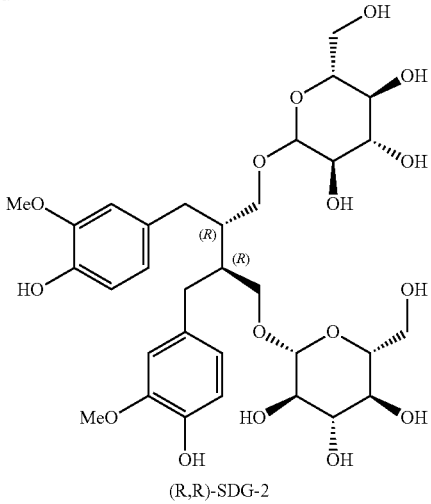

(R,R)-SDG-2

Example 6: Synthesis of Glycosidated Isomers (S,S)-S3 and (R,R)-S4

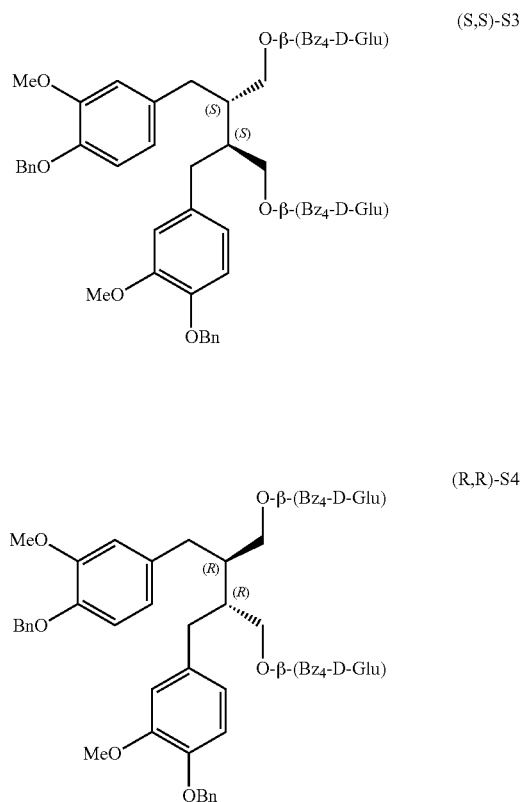

A flask was charged with diol 6 (0.408 g, 0.751 mmol, 1 equiv) and trichloroacetimidate 7[3] (1.67 g, 2.25 mmol, 3 equiv) and dried by benzene azeotrope (3×10 mL). Activated 4 Å molecular sieves (0.800 g) and $CH_2Cl_2$ (7.5 mL) were added and the solution was stirred for 1 h. After cooling to −40° C., TMSOTf (54 μL, 0.300 mmol, 0.4 equiv) was added dropwise and the reaction mixture was allowed to warm to 25° C. overnight. The next morning, $NEt_3$ (200 μL) was added and the mixture was filtered through a silica pad (1 in, washing with EtOAc) and concentrated. The resulting crude was purified by flash column chromatography (silica, 9:1:1→8:2:1→7:2:2 hexanes:EtOAc:$CH_2Cl_2$) to give a 1:1 inseparable mixture of diastereomers (S,S)-S3 and (R,R)-S4 (1.128 g, 0.664 mmol, 88% yield). (S,S)-S3/(R,R)-S4: $R_f$=0.22 (silica, 7:2:1 hexanes:EtOAc:$CH_2Cl_2$); IR (film): $v_{max}$=2941, 1727, 1601, 1511, 1451, 1262, 1092, 1026, 708 $cm^{-1}$; $^1H$ NMR (600 MHz, $CDCl_3$) δ=8.04 (d, J=7.70 Hz, 4H), 8.01 (d, J=7.62 Hz, 4H), 7.98-7.91 (m, 12H), 7.87-7.81 (m, 12H), 7.57-7.26 (m, 68H), 6.61 (d, J=8.26 Hz, 2H), 6.49 (s, 2H), 6.44 (d, J=8.0 Hz, 2H), 6.42-6.38 (m, 4H), 6.23 (d, J=8.14 Hz, 2H), 5.93 (t, J=10.07 Hz, 2H), 5.81 (t, J=9.68 Hz, 2H), 5.72 (t, J=10.07 Hz, 2H), 5.67 (t, J=9.68 Hz, 2H), 5.56 (t, J=7.72 Hz, 2H), 5.45 (t, J=8.24 Hz, 2H), 5.08 (s, 8H), 4.72 (dd, J=12.19, 2.70 Hz, 2H), 4.66 (d, J=8.22 Hz, 2H), 4.61 (dd, J=12.19, 3.08 Hz, 2H), 4.49-4.42 (m, 4H), 4.39 (d, J=7.70 Hz, 2H), 4.14-4.08 (m, 2H), 3.98-3.93 (m, 2H), 3.92-3.87 (m, 2H), 3.74 (s, 6H), 3.70 (s, 6H), 3.65-3.61 (m, 2H), 3.40-3.34 (m, 2H), 3.24-3.18 (m, 2H), 2.56-2.45 (m, 6H), 2.41-2.34 (m, 2H), 1.85 (s, 2H), 1.73 (s, 2H) ppm; $^{13}C$ NMR (150 MHz, $CDCl_3$) δ=166.20, 166.19, 165.93, 165.90, 165.29, 165.16, 164.98, 149.38, 149.35, 146.32, 146.20, 137.56, 133.73, 133.66, 133.56, 133.53, 133.45, 133.37, 133.34, 133.28, 129.93, 129.91, 129.86, 129.84, 129.76, 129.66, 129.64, 129.38, 129.30, 128.95, 128.92, 128.91, 128.60, 128.58, 128.55, 128.53, 128.42, 127.83, 127.81, 127.39, 127.32, 121.38, 121.19, 113.61, 112.70, 112.51, 101.31, 101.23, 73.06, 72.93, 72.12, 72.10, 72.06, 71.99, 71.05, 71.00, 69.89, 69.81, 69.61, 69.32, 63.07, 62.98, 55.94, 55.93, 41.00, 40.78, 35.35, 35.14 ppm; HRMS (ESI-TOF): calcd for $C_{102}H_{90}O_{24}$ [M+H$^+$]: 1699.5895, found 1699.5917.

Example 7: Phenols (S,S)-8 and (R,R)-9

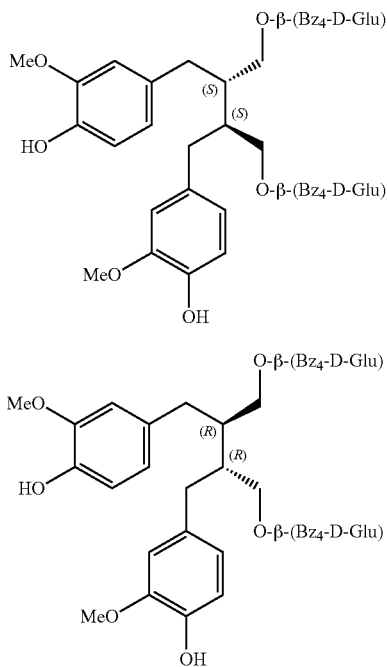

The 1:1 mixture of (S,S)-S3 and (R,R)-S4 (0.612 g, 0.360 mmol, 1 equiv) in EtOAc (3.6 mL) was saturated with an argon atmosphere by briefly exposing to vacuum and backfilling with argon several times. Palladium on carbon (10% Pd by weight, 0.120 g) was added and the solution was saturated with $H_2$ by vacuum/backfill $H_2$. After stirring at 25° C. for 36 h, the solution was put under an argon atmosphere, filtered through a pad of Celite (1.5 in, washing with EtOAc and $CH_2Cl_2$), and the filtrate concentrated. The resulting solid was dissolved in a small amount of $CH_2Cl_2$ and purified by flash column chromatography (silica, 3:7→4:6→5:5 EtOAc:hexanes) to give the debenzylated glycoside (0.470 g, 0.309 mmol, 86% yield) as a 1:1 mixture of diastereomers. The diastereomers could be separated by preparative thin-layer chromatography (silica, 2 mm, multiple plates, 7:20 EtOAc:hexanes, >10 elution runs) to give (S,S)-8 and (R,R)-9 as off-white solids. (S,S)-8: $R_f$=0.10 (4:6 EtOAc:hexanes); $[\alpha]_D^{32}$=+1.2 (EtOAc, c=4.3); IR (film): $v_{max}$=3460, 2938, 1729, 1514, 1451, 1265, 1023, 1061, 1027, 709 cm$^{-1}$; $^1$H NMR (600 MHz, CDCl$_3$) δ=8.03 (d, J=8.42 Hz, 4H), 7.92 (d, J=8.22 Hz, 4H), 7.83 (d, J=7.48 Hz, 8H), 7.58-7.46 (m, 6H), 7.45-7.27 (m, 18H), 6.62 (d, J=7.90 Hz, 2H), 6.43 (dd, J=7.90, 1.16 Hz, 2H), 6.38 (d, J=1.16 Hz, 2H), 5.80 (t, J=9.57 Hz, 2H), 5.64 (t, J=9.57 Hz, 2H), 5.44 (t, J=9.74 Hz, 2H), 5.40 (s, 2H), 4.62 (dd, J=12.09, 2.98 Hz, 2H), 4.44 (dd, J=12.09, 5.17 Hz, 2H), 4.41 (d, J=8.03 Hz, 2H), 3.96 (m, 2H), 3.69 (s, 6H), 3.64 (dd, J=9.38, 2.82 Hz, 2H), 3.21 (dd, J=9.43, 4.13 Hz, 2H), 2.48 (d, J=6.8 Hz, 4H), 1.71 (s, 2H) ppm; $^{13}$C NMR (150 MHz, CDCl$_3$) δ=166.26, 165.92, 165.35, 165.05, 146.27, 143.64, 133.60, 133.49, 133.38, 133.37, 132.41, 129.95, 129.88, 129.85, 129.78, 129.67, 129.30, 128.94, 128.60, 128.57, 128.45, 122.01, 113.83, 111.49, 101.37, 72.96, 72.15, 72.00, 69.89, 69.54, 63.16, 55.82, 40.87, 35.26 ppm; HRMS (ESI-TOF): calcd for $C_{88}H_{78}O_{24}$ [M+H$^+$]: 1519.4956, found 1519.4937.

(R,R)-9: $R_f$=0.10 (4:6 EtOAc:hexanes); $[\alpha]_D^{32}$=+4.8 (EtOAc, c=4.1); IR (film): $v_{max}$=3457, 2942, 1726, 1262, 1026, 707 cm$^{-1}$; $^1$H NMR (600 MHz, CDCl$_3$) δ=8.00 (d, J=7.62 Hz, 4H), 7.97 (d, J=7.71 Hz, 4H), 7.93 (d, J=7.98 Hz, 4H), 7.62 (d, J=7.71 Hz, 4H), 7.56-7.27 (m, 24H), 6.45 (d, J=7.95 Hz, 2H), 6.29 (s, 2H), 6.24 (d, J=7.95 Hz, 2H), 5.91 (t, J=9.82 Hz, 2H), 5.70 (t, J=9.67 Hz, 2H), 5.54 (t, J=9.23 Hz, 2H), 5.40 (s, 2H), 4.71 (dd, J=11.87, 3.29 Hz, 2H), 4.62 (d, J=7.92 Hz, 2H), 4.42 (dd, J=12.14, 4.72 Hz, 2H), 4.11-4.06 (m, 2H), 3.85 (dd, J=9.53, 3.46 Hz, 2H), 3.65 (s, 6H), 3.34 (dd, J=9.70, 4.68 Hz, 2H), 2.47-2.40 (m, 2H), 2.37-2.30 (m, 2H), 1.82 (s, 2H) ppm; $^{13}$C NMR (150 MHz, CDCl$_3$) δ=166.23, 165.95, 165.34, 165.21, 146.33, 143.54, 133.56, 133.50, 133.36, 133.30, 132.44, 129.96, 129.92, 129.87, 129.65, 129.42, 128.98, 128.66, 128.55, 128.44, 121.98, 113.66, 111.12, 101.25, 73.07, 72.15, 72.08, 69.88, 69.78, 62.97, 55.78, 40.67, 35.50 ppm; HRMS (ESI-TOF): calcd for $C_{36}H_{38}O_8$ [M+H$^+$]: 1519.4956, found 1519.4947.

Example 8: Synthesis of Secoisolariciresinol Diglucoside (S,S)-SDG-1

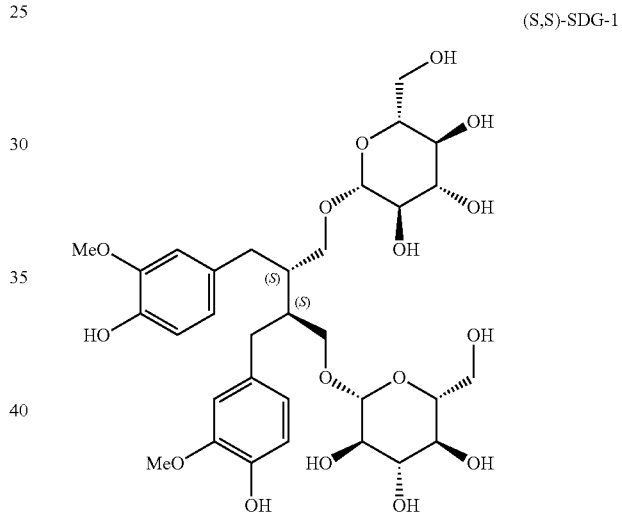

To a flask containing dry (S,S)-8 (0.043 g, 0.028 mmol, 1 equiv), a freshly prepared solution of NaOMe in MeOH (0.4 M, 2 mL, 28 equiv) was added and the solution was stirred for 60 h at 25° C. The solution was then filtered through a pad of silica (0.5 in, washing with MeOH) and the filtrate was concentrated. The resulting solid was purified by preparative thin-layer chromatography (silica, 2 mm, 9:1→7:3 $CH_2Cl_2$:MeOH, then 5:5 $CH_2Cl_2$:MeOH half of plate length) and then passed through a small plug of reversed phase silica (100 Å, $C_{18}$) to provide (S,S)-SDG-1 (0.017 g, 0.025 mmol, 88% yield) as an off-white solid. (S,S)-SDG-1: $R_f$=0.57 (silica, 1:1 $CH_2Cl_2$:MeOH); $[\alpha]_D^{32}$=−0.3 (MeOH, c=1.2); IR (film): $v_{max}$=3340, 2950, 1601, 1515, 1372, 1270, 1070, 1015, 798 cm$^{-1}$; $^1$H NMR (600 MHz, CDCl$_3$) δ=6.65 (d, J=8.05 Hz, 2H), 6.59 (d, J=1.31 Hz, 2H), 6.56 (dd, J=8.05, 1.31 Hz, 2H), 4.24 (d, J=7.42 Hz, 2H), 4.08 (dd, J=10.09, 5.58 Hz, 2H), 3.85 (dd, J=12.00, 2.43 Hz, 2H), 3.73 (s, 6H), 3.69 (dd, J=11.85, 5.55 Hz, 4H), 3.50-3.45 (m, 2H), 3.38-3.28 (m, 4H), 3.27-3.19 (m, 4H), 2.69 (dd, J=13.82, 6.72 Hz, 2H), 2.61 (dd, J=13.82, 7.98 Hz, 2H), 2.12 (m, 2H) ppm; $^{13}$C NMR (150 MHz, CDCl$_3$) δ=148.69, 145.35, 133.93, 122.89, 115.63, 113.51, 104.77, 78.16, 77.89, 75.25, 71.69, 71.18, 62.79, 56.25, 41.20, 35.60 ppm; HRMS (ESI-TOF): calcd for $C_{32}H_{46}O_{16}[M+H^+]$: 687.2858, found 687.2856.

Example 9: Synthesis of Secoisolariciresinol Diglucoside(R,R)-SDG-2

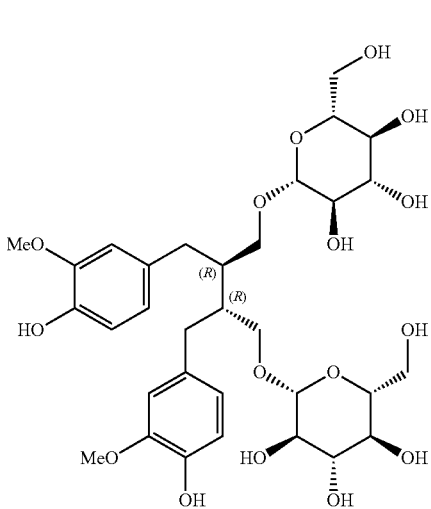

(R,R)-SDG-2

To a flask containing dry (R,R)-9 (0.041 g, 0.027 mmol, 1 equiv), a freshly prepared solution of NaOMe in MeOH (0.4 M, 2 mL, 28 equiv) was added and the solution stirred for 60 h at 25° C. The solution was then filtered through a pad of silica (0.5 in, washing with MeOH) and the filtrate concentrated. The resulting solid was purified by preparative thin-layer chromatography (silica, 2 mm, 9:1→7:3 $CH_2Cl_2$:MeOH, then 5:5 $CH_2Cl_2$:MeOH half of plate length) and then passed through a small plug of reversed phase silica (100 Å $C_{18}$, washing with MeOH) to provide (R,R)-SDG-2 (0.015 g, 0.022 mmol, 81% yield) as an off-white solid. (R,R)-SDG-2: $R_f$=0.50 (silica, 1:1 $CH_2Cl_2$:MeOH); $[\alpha]_D^{32}$=−22.2 (MeOH, c=1.0); IR (film): $v_{max}$=3336, 2949, 1651, 1409, 1014 cm$^{-1}$; $^1$H NMR (600 MHz, CDCl$_3$) δ=6.66 (d, J=8.06 Hz, 2H), 6.64 (d, J=1.63 Hz, 2H), 6.59 (dd, J=8.06, 1.63 Hz, 2H), 4.21 (d, J=7.82 Hz, 2H), 3.91 (dd, J=10.11, 5.69 Hz, 2H), 3.87 (dd, J=12.01, 2.01 Hz, 2H), 3.75 (s, 6H), 3.67 (dd, J=12.02, 5.47 Hz, 2H), 3.58 (dd, J=9.90, 5.36 Hz, 2H), 3.38-3.18 (m, 8H), 2.76-2.62 (m, 4H), 2.14-2.07 (m, 2H) ppm; $^{13}$C NMR (150 MHz, CDCl$_3$) δ=148.77, 145.37, 134.05, 122.83, 115.70, 113.56, 104.59, 78.19, 77.93, 75.19, 71.70, 70.62, 62.79, 56.32, 41.63, 35.62 ppm; HRMS (ESI-TOF): calcd for $C_{32}H_{46}O_{16}$ [M+H$^+$]: 687.2858, found 687.2856.

Methods for Biological Assays

Assay Kits

HORAC Assay kit (#TA30) was purchased from Oxford Biomedical Research. ORAC Assay kit (#STA345) was obtained from Cell Biolab, San Diego, Calif. SDG standard was purchased from Chromadex Inc., San Diego, Calif.

Reducing Power Activity Assay

The determination of reducing power was performed as described by Yen and Der (*J. Am. Oil Chem. Soc.* 1993, 70, 383). Reducing power assay determines the reducing potential of the test compound which reacts with potassium ferricyanide (Fe$^{+3}$) to form potassium ferrocyanide (Fe$^{+2}$), which subsequently reacts with ferric chloride to produce a ferric-ferrous complex that has maximum absorption at 700 nm. Various concentrations (1-500 μM) of test compounds were taken in sodium phosphate buffer (0.1 M, pH 6.6) in 96-well microplates and mixed with potassium ferricyanide (1%). Samples were incubated at 50° C. and equal volume of 10% trichloroacetic acid was added. The upper layer was mixed with deionized water (1:1:2) and ferric chloride (0.1%). The absorbance was read at 700 nm on a Bio-Rad microplate reader (Bio-Rad, Hercules, Calif.). The increase in absorbance indicates increase in reducing power.

Hydroxyl Radical Scavenging Potential (HORAC Assay)

The ability of SDGs to scavenge hydroxyl radicals in a chemical system was evaluated using HORAC Assay kit (#TA30) obtained from Oxford Biomedical Research. Hydroxyl radicals were generated from hydrogen peroxide by Fenton reaction. Oxidation of fluorescein was measured on a fluorescence microplate reader. Antioxidants inhibit fluorescein oxidation. Gallic acid was used as a standard for calibration curve. Calculations used SDG concentration that fit the linear part of the calibration curve. SDG concentrations were used in the range of 8 μM-1 mM. Antioxidant capacity against hydroxyl radicals was expressed as gallic acid equivalent (GAE).

Peroxyl Radical Scavenging Potential (ORAC ASSAY)

The ability of SDGs to scavenge peroxyl radicals in a chemical system was evaluated using an ORAC assay kit (#STA345) obtained from Cell Biolab (San Diego, Calif.). Peroxyl radicals were generated by AAPH (2,2'-azobis(2-amidinopropanedihydrochloride). Oxidation of fluorescein was measured using a fluorescence microplate reader. Antioxidants inhibit fluorescein oxidation. Trolox was used as a standard for calibration curve. Calculations used SDG concentrations that fit the linear part of the calibration curve. SDG concentrations were used in the range of 8 μM-1 mM. Antioxidant capacity against peroxyl radicals was expressed as Trolox equivalent (TE).

DPPH Radical Scavenging Assay.

The ability of the SDGs to scavenge DPPH radicals was assessed as described by Moree et al. (*Free Rad. Antiox.* 2011, 1, 31) with minor modifications for use in microplates. Briefly, different concentrations of SDG isomers and other test compounds were incubated with 200 μL medium in 96-well microplates containing 0.1 M Tris buffer (pH 7.4) and 250 μM DPPH solution, and kept in the dark for 20 min. The absorbance was read at 517 nm in a Bio-Rad microplate reader. Ascorbic acid and α-tocopherol were used as known antioxidants for comparison. The radical scavenging activity was measured as a decrease in the absorbance of DPPH and calculated using the following equation: Percentage inhibition=[O.D.$_{control}$−O.D.$_{treated}$/O.D.$_{control}$]×100.

Example 10: Reducing Powers of (S,S)-SDG-1 and (R,R)-SDG-2

Figure 2:
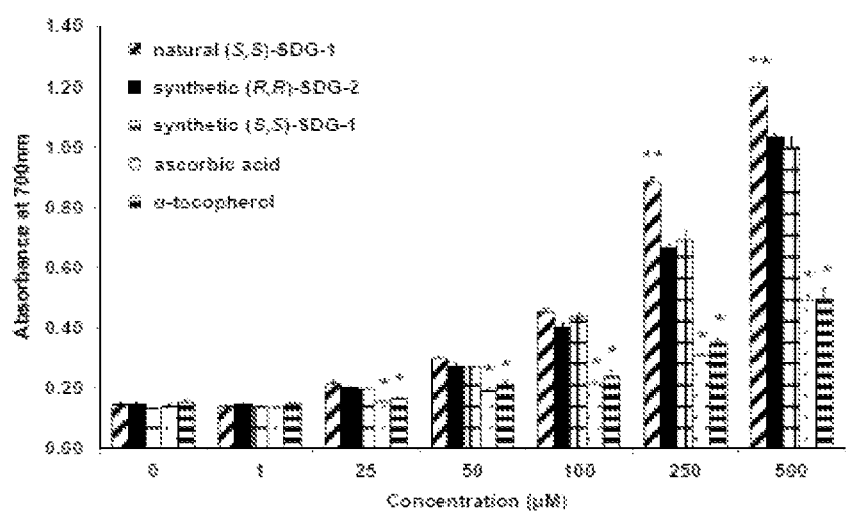
FIG. 2 illustrates the reducing power of synthetic (S,S)-SDG-1 and (R,R)-SDG-2. The increase in absorbance at 700 nm indicates increase in reducing power. The results are presented as mean±standard deviation (n=3). *$p<0.05$ significantly lower than natural (S,S)-SDG-1, synthetic (R,R)-SDG-2, and synthetic (S,S)-SDG-1; **$p<0.05$ significantly higher than synthetic (R,R)-SDG-2, synthetic (S,S)-SDG-1, ascorbic acid and α-tocopherol.
Figure 3:
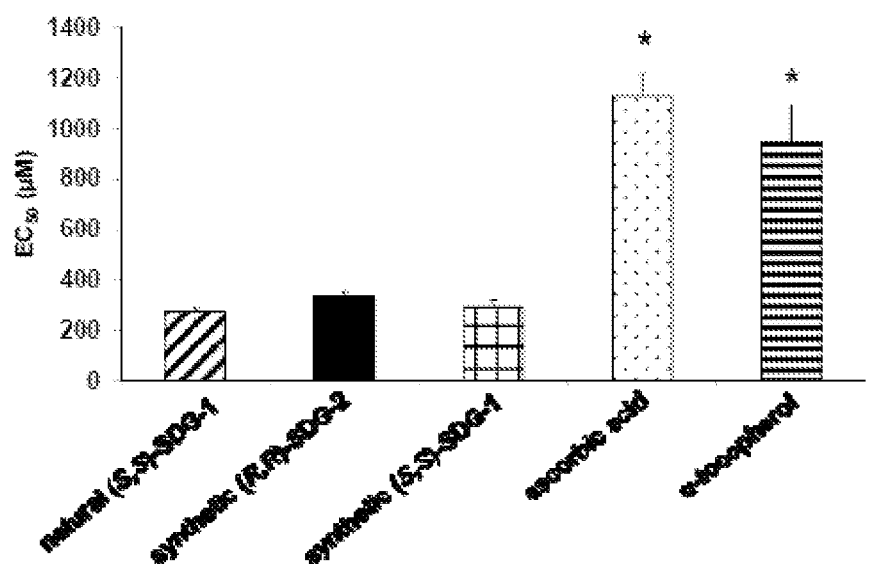
FIG. 3 illustrates the reducing power of synthetic (S,S)-SDG-1 and (R,R)-SDG-2. The rate of reaction is linear in the concentration range of 1-100 μM. Equation of the linear regression was used to determine $EC_{50}$. The results are presented as mean±standard deviation (n=3). Natural (S,S)-SDG-1, synthetic (R,R)-SDG-2, and synthetic (S,S)-SDG-1 were not significantly different from each other. *$p<0.05$ significantly higher than natural (S,S)-SDG-1, synthetic (R,R)-SDG-2, and synthetic (S,S)-SDG-1.

The reducing powers of synthetic (S,S)-SDG-1, synthetic (R,R)-SDG-2, natural (S,S)-SDG-1, ascorbic acid, and α-tocopherol were determined by the reduction of $K_3FeCN_6$ in the presence of $FeCl_3$, as measured by the absorbance of the resulting ferric-ferrous complex (FIG. 2). The reducing power of synthetic (S,S)-SDG-1, synthetic (R,R)-SDG-2, and natural (S,S)-SDG-1 were significantly concentration dependent at higher concentrations; however, at all concentrations tested the SDGs had comparable or higher reducing power than known antioxidants ascorbic acid and α-tocopherol, with a notable increase in potency in the 200-500 μM range. A linear relationship between reducing power and substrate concentration was observed at lower concentrations (1-100 µM), allowing regression line equations to be established for the five compounds. This allowed the half maximal effective concentration ($EC_{50}$) for reducing power to be calculated (FIG. 3). The $EC_{50}$ (mean±std. dev.) values for (S,S)-SDG-1 and (R,R)-SDG-2 were 292.17±27.71 µM and 331.94±21.21 µM, respectively. These values were comparable to that of natural (S,S)-SDG-1 ($EC_{50}$=275.24±13.15 µM) but approximately three-fold higher than that exhibited by ascorbic acid ($EC_{50}$=1129.32±88.79 µM) and α-tocopherol ($EC_{50}$=944.62±148.00 µM).

Example 11: The Ability to Scavenge Hydroxyl and Peroxyl Radicals

The ability of synthetic (S,S)-SDG-1 and (R,R)-SDG-2 to scavenge hydroxyl and peroxyl radicals as manifested by their inhibition of the oxidation of fluorescein was assessed by the hydroxyl radical averting capacity (HORAC, gallic acid standard) and peroxyl radical absorbance capacity assays (ORAC, trolox standard), respectively (Table 1). Fluorescein oxidation by hydroxyl radicals was decreased by synthetic (S,S)-SDG-1 and synthetic (R,R)-SDG-2 in a concentration-dependent manner and was found to be two-fold higher than gallic acid. However, synthetic (S,S)-SDG-1 activity differed from natural (S,S)-SDG-1, likely due to trace impurities. Fluorescein oxidation by peroxyl radicals generated using 2,2'-azobis(2-amidinopropane) dihydrochloride (AAPH) was greatly reduced in the presence of synthetic (S,S)-SDG-1, (R,R)-SDG-2 and natural (S,S)-SDG-1, with a two-fold increase in potency over the trolox standard (Table 1).

TABLE 1

Antioxidant Capacity of Synthetic and Natural SDGs

| Entry | Antioxidant | Against Hydroxyl[a] Radicals (GAE)[c] | Against Peroxyl[b] Radicals (TE)[d] |
|---|---|---|---|
| 1. | natural (S,S)-SDG-1 | 3.68 ± 0.27 | 2.55 ± 0.11 |
| 2. | synthetic (R,R)-SDG-2 | 1.96 ± 0.27 | 2.20 ± 0.10 |
| 3. | synthetic (S,S)-SDG-1 | 2.09 ± 0.16 | 3.03 ± 0.04 |

[a]Determined by HORAC Assay;
[b]Determined by ORAC Assay;
[c]Gallic acid equivalent;
[d]Trolox equivalents.

In Table 1, hydroxyl radicals were generated from hydrogen peroxide by Fenton reaction. Peroxyl radicals were generated by AAPH (2,2'-azobis(2-amidinopropane) dihydrochloride). Oxidation of fluorescein was measured. Calculations used SDG concentrations that fitted the linear part of the calibration curve. The results are presented as mean±standard deviation (n=3).

Example 12: Free Radical Scavenging Activities of (S,S)-SDG-1 and (R,R)-SDG-2

Figure 4:
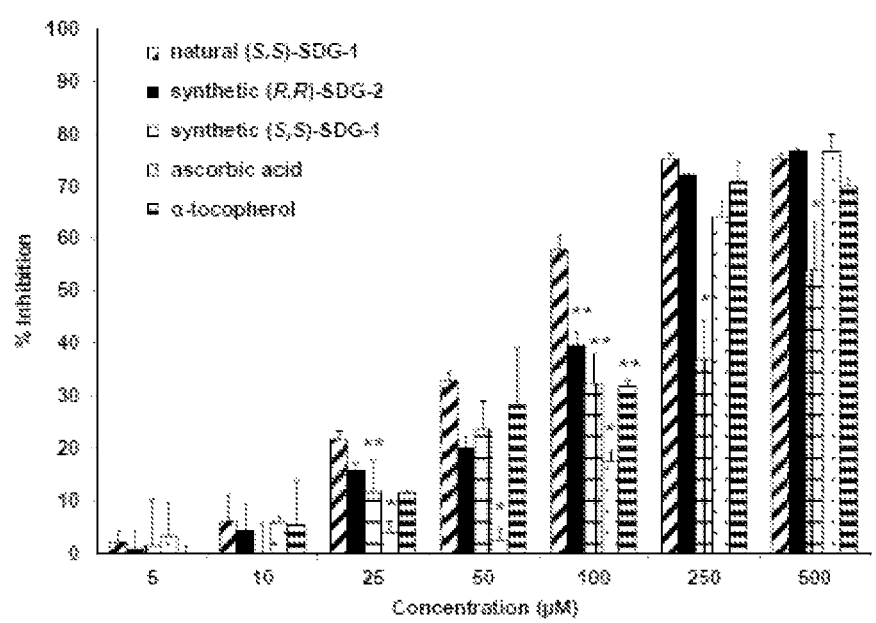
FIG. 4 depicts DPPH free radical scavenging activity of natural (S,S)-SDG-1, synthetic (S,S)-SDG-1 and (R,R)-SDG-2, ascorbic acid, and α-tocopherol. The radical scavenging activity was measured as a decrease in the absorbance of DPPH at 517 nm. The results are presented as mean±standard deviation (n=3). *$p<0.05$ significantly lower than all other compounds, **$p<0.05$ significantly lower than natural (S,S)-SDG-1.
Figure 5:
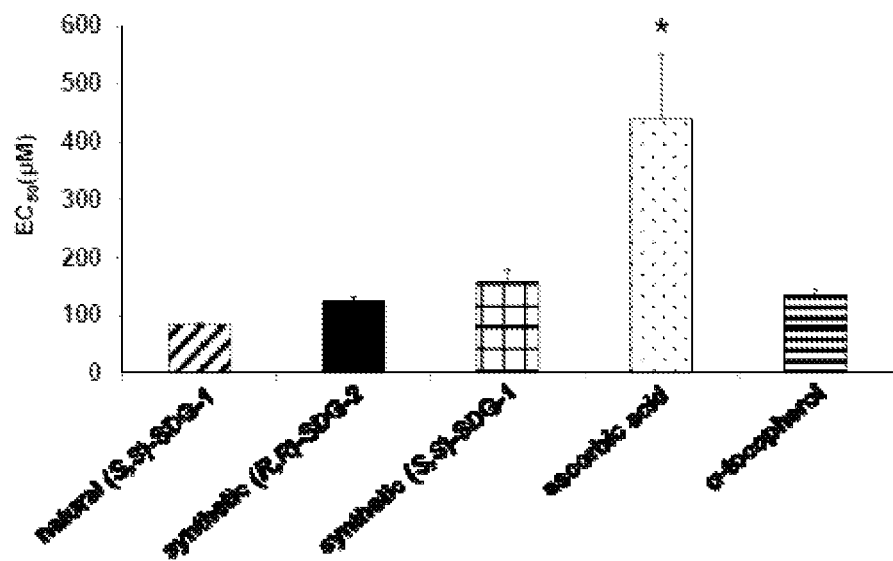
FIG. 5 depicts DPPH free radical scavenging activity of natural (S,S)-SDG-1, synthetic (S,S)-SDG-1 and (R,R)-SDG-2, ascorbic acid, and α-tocopherol. Equation of the linear regression was used to determine $EC_{50}$. The rate of reaction is linear in the concentration range of 1-100 μM. The results are presented as mean±standard deviation (n=3). Natural (S,S)-SDG-1, synthetic (R,R)-SDG-2, synthetic (S,S)-SDG-1, and α-tocopherol were not significantly different. *$p<0.05$ significantly higher than natural (S,S)-SDG-1, synthetic (R,R)-SDG-2, synthetic (S,S)-SDG-1, and α-tocopherol.
Figure 6:
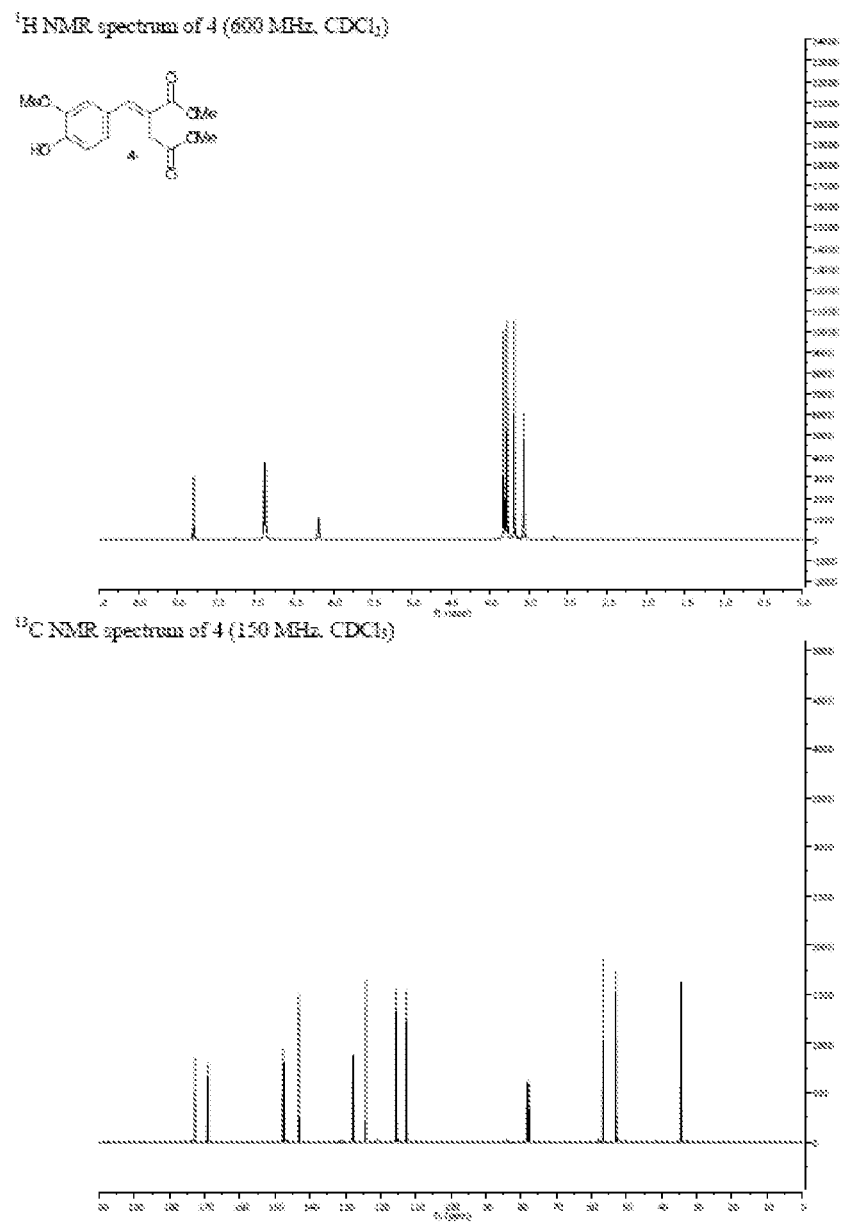
FIG. 6 shows $^1$H NMR (600 MHz, CDCl$_3$) and $^{13}$C NMR (150 MHz, CDCl$_3$) spectra of compound 4.
Figure 7:
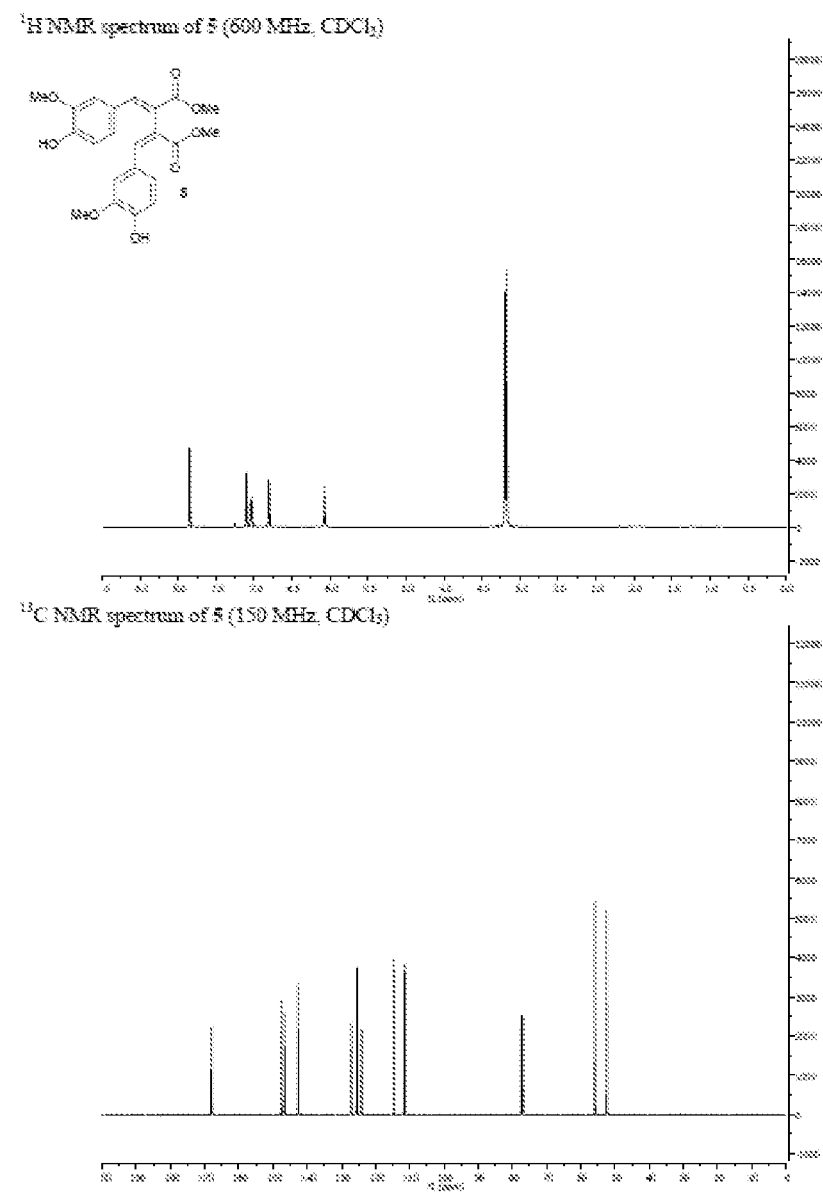
FIG. 7 shows $^1$H NMR (600 MHz, CDCl$_3$) and $^{13}$C NMR (150 MHz, CDCl$_3$) spectra of compound 5.
Figure 8:
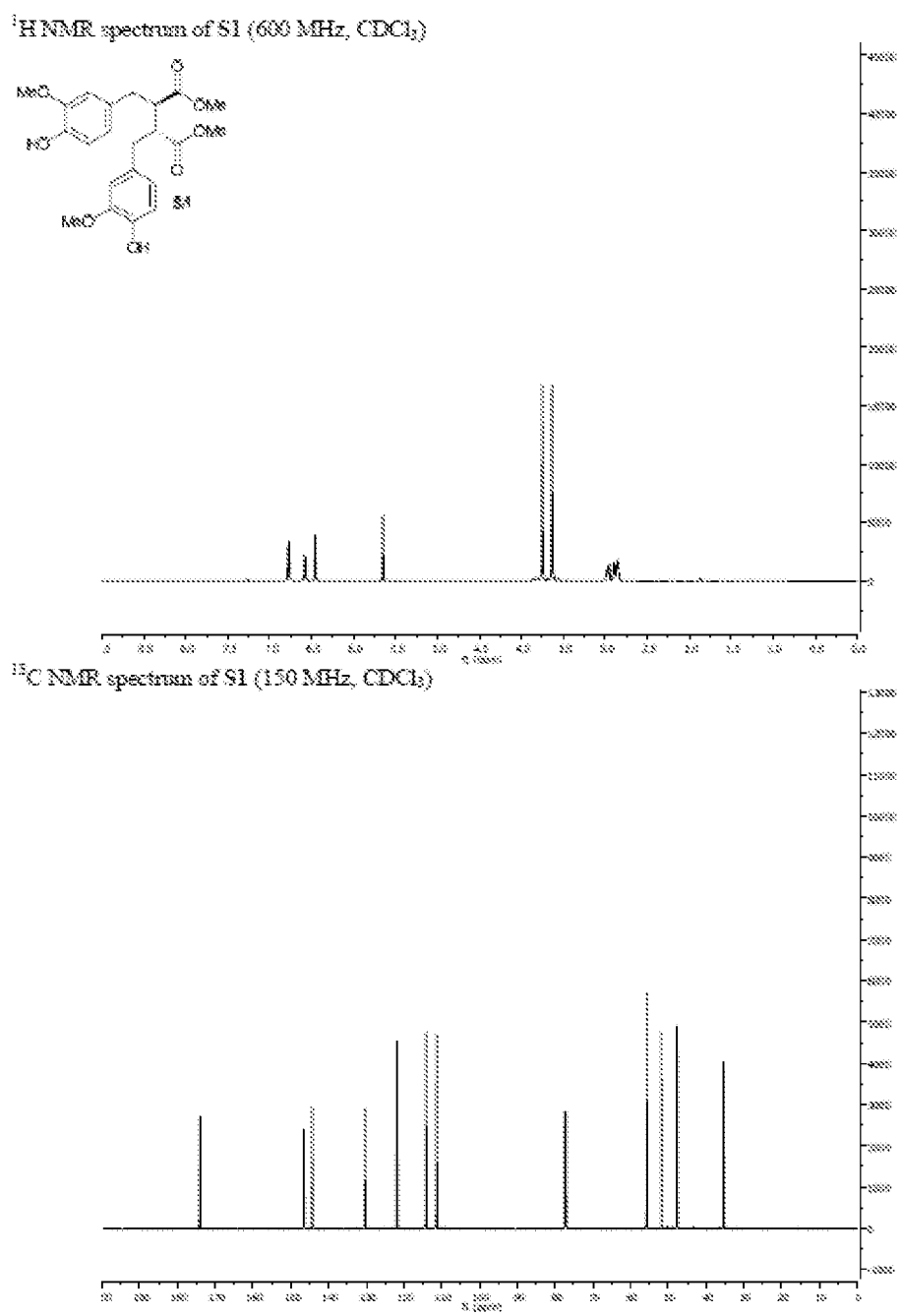
FIG. 8 shows $^1$H NMR (600 MHz, CDCl$_3$) and $^{13}$C NMR (150 MHz, CDCl$_3$) spectra of compound S1.
Figure 9:
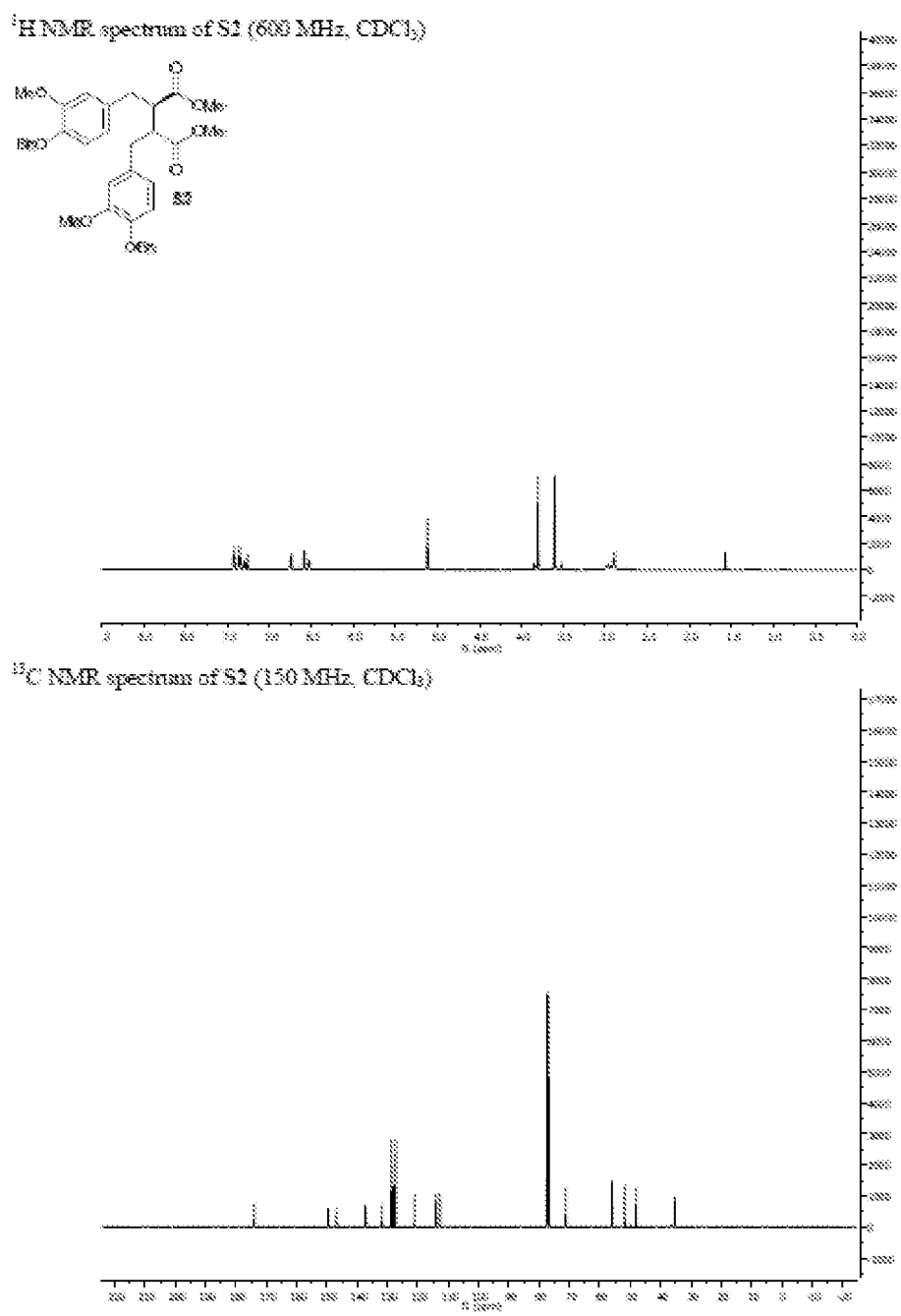
FIG. 9 shows $^1$H NMR (600 MHz, CDCl$_3$) and $^{13}$C NMR (150 MHz, CDCl$_3$) spectra of compound S2.
Figure 10:
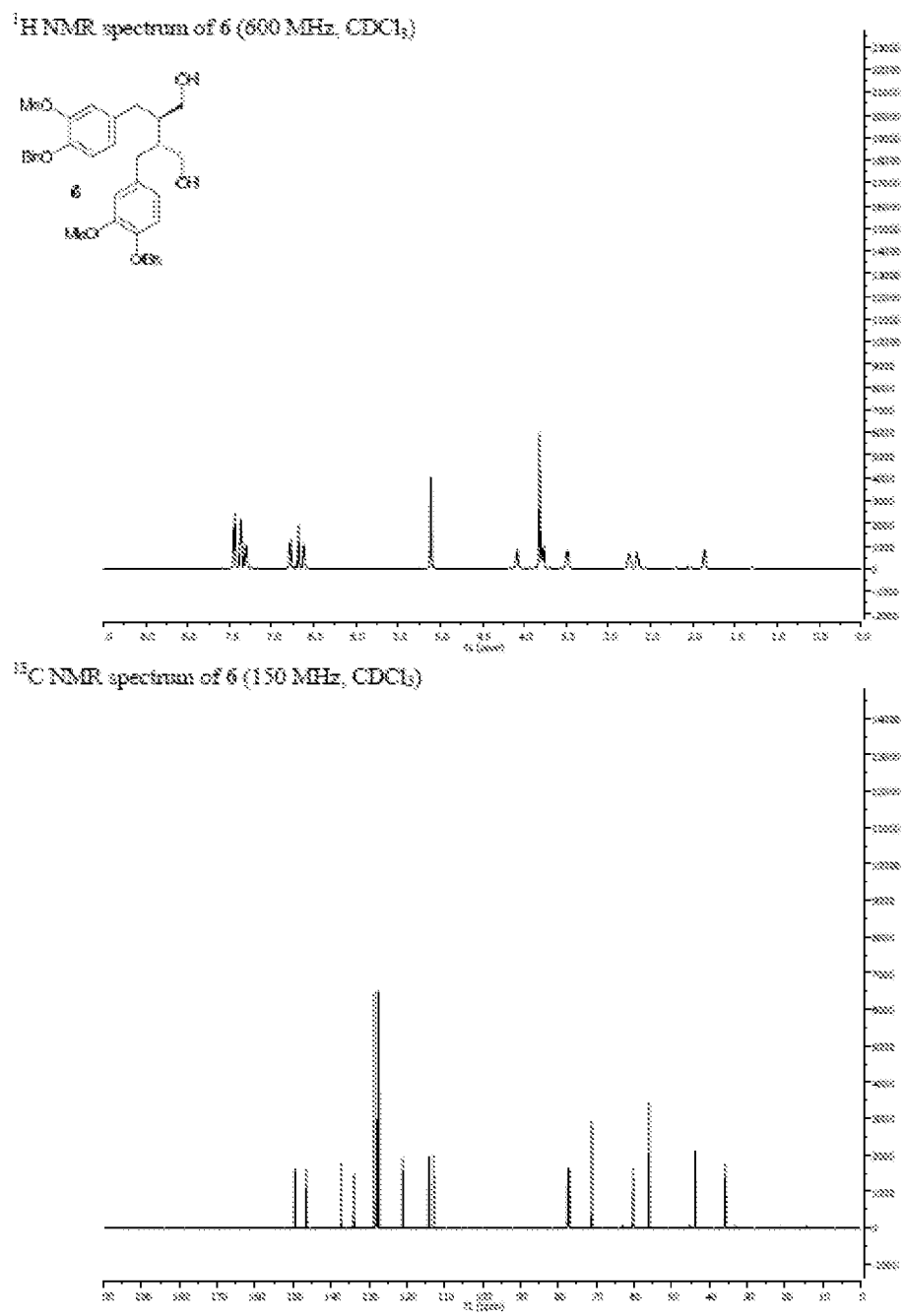
FIG. 10 shows $^1$H NMR (600 MHz, CDCl$_3$) and $^{13}$C NMR (150 MHz, CDCl$_3$) spectra of compound 6.
Figure 11:
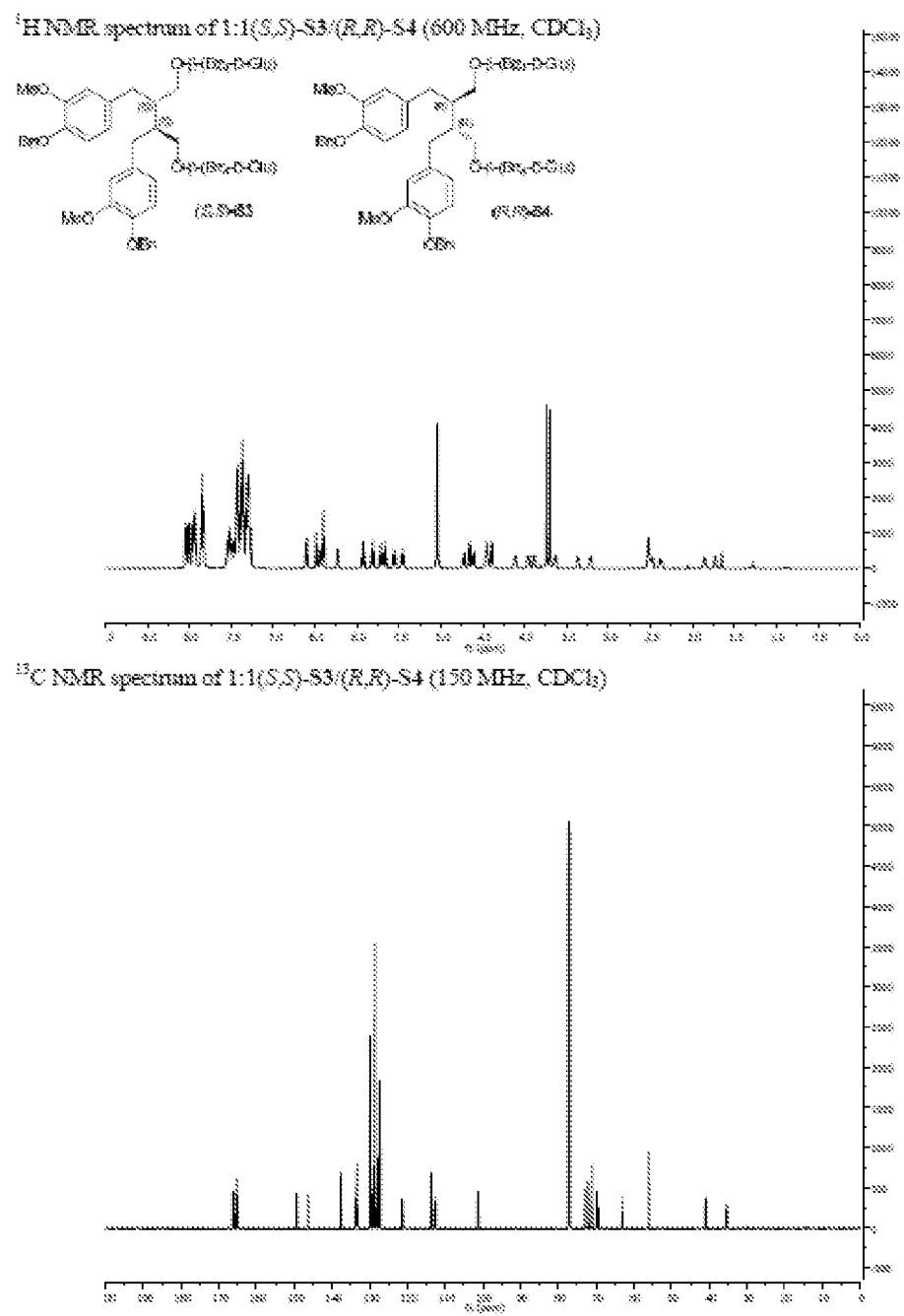
FIG. 11 shows $^1$H NMR (600 MHz, CDCl$_3$) and $^{13}$C NMR (150 MHz, CDCl$_3$) spectra of 1:1 (S,S)-S3/(R,R)-S4.
Figure 12:
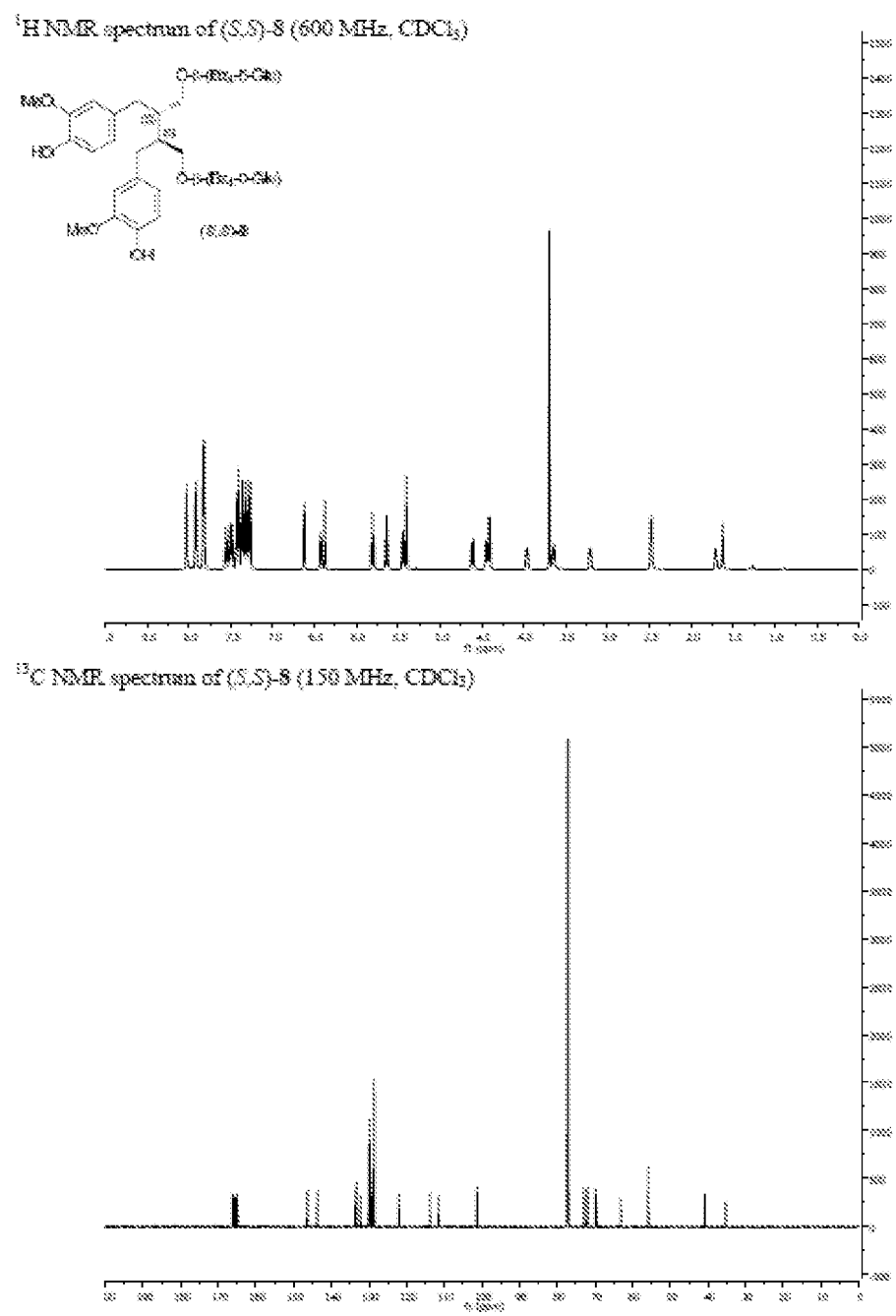
FIG. 12 shows $^1$H NMR (600 MHz, CDCl$_3$) and $^{13}$C NMR (150 MHz, CDCl$_3$) spectra of compound (S,S)-8.
Figure 13:
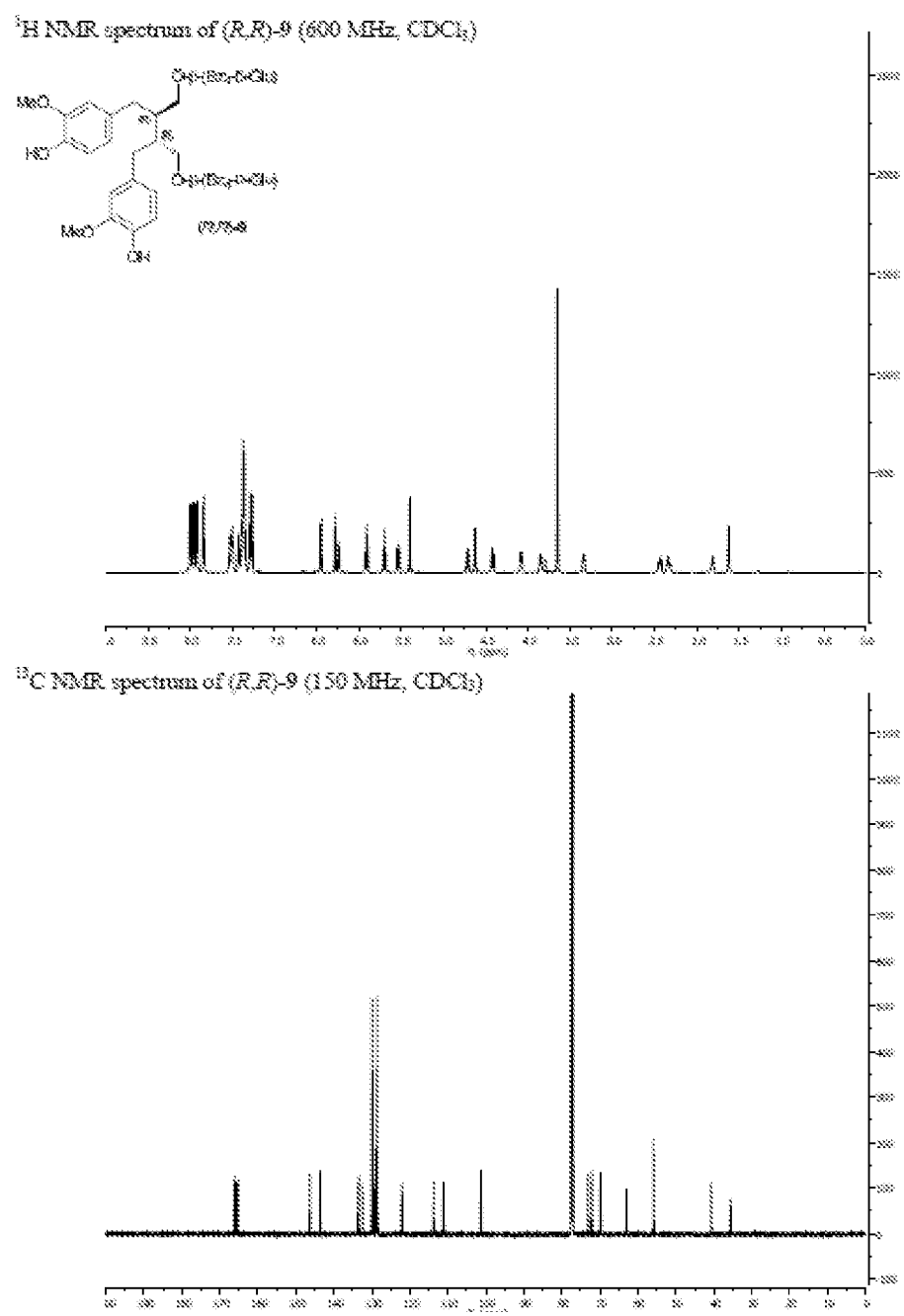
FIG. 13 shows $^1$H NMR (600 MHz, CDCl$_3$) and $^{13}$C NMR (150 MHz, CDCl$_3$) spectra of compound (R,R)-9.
Figure 14:
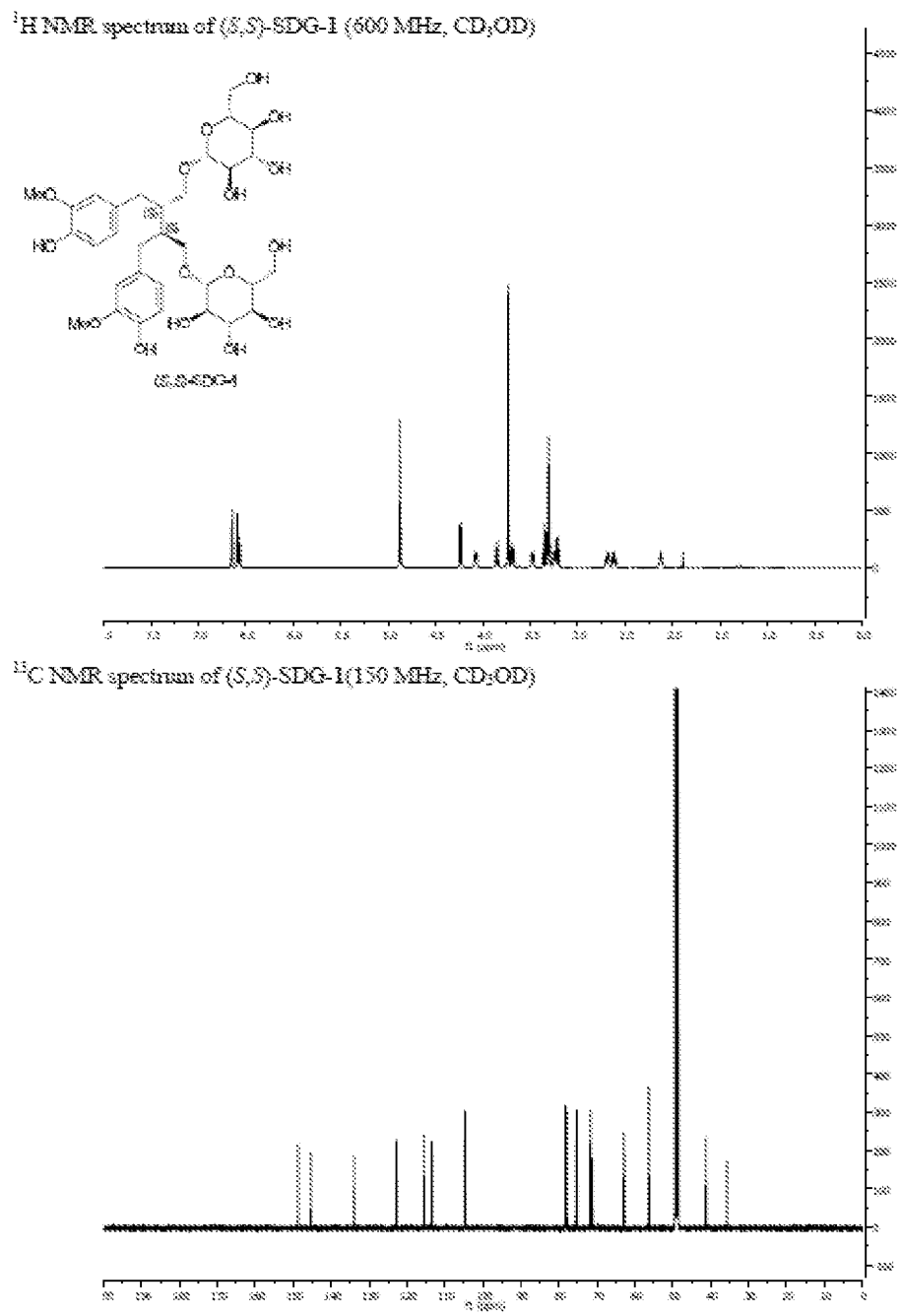
FIG. 14 shows $^1$H NMR (600 MHz, CD$_3$OD) and $^{13}$C NMR (150 MHz, CD$_3$OD) spectra of compound (S,S)-SDG-1.
Figure 15:
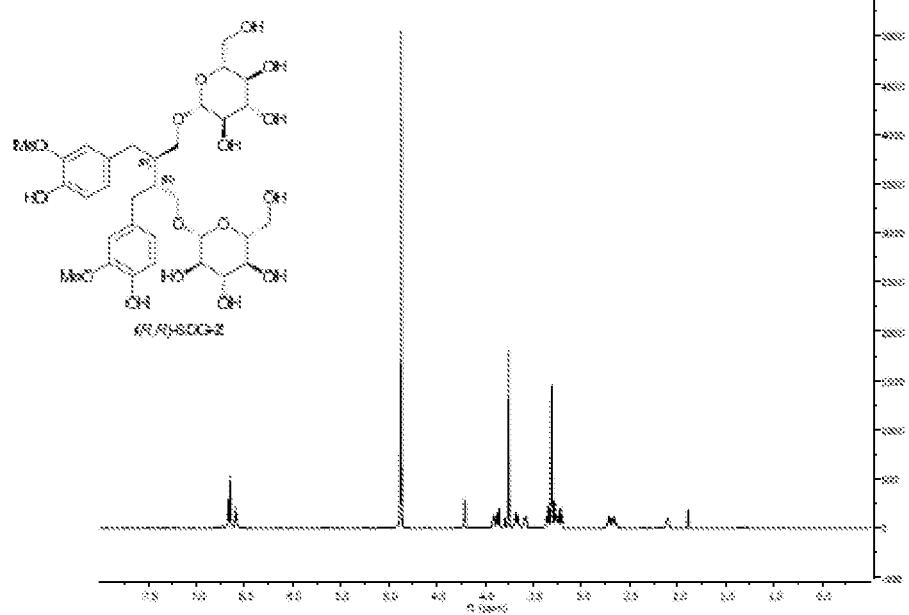
FIG. 15 shows $^1$H NMR (600 MHz, CD$_3$OD) and $^{13}$C NMR (150 MHz, CD$_3$OD) spectra of compound (R,R)-SDG-2.
Figure 15:
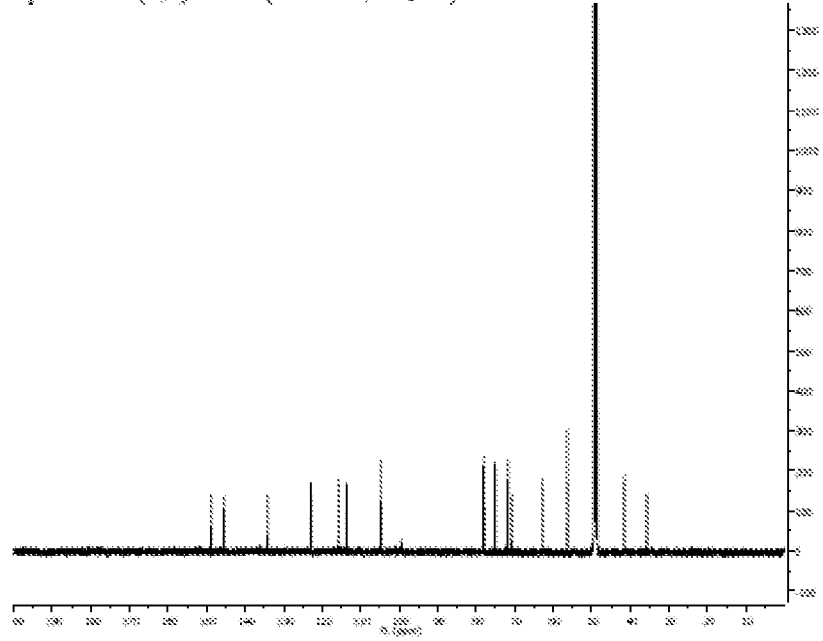

The free radical scavenging activities of synthetic (S,S)-SDG-1 and (R,R)-SDG-2 were determined using a 2,2-diphenyl-1-picrylhydrazyl (DPPH) free radical scavenging assay and was compared to those of natural (S,S)-SDG-1, ascorbic acid, and α-tocopherol (FIG. 4). At low (5-25 µM) and mid-concentration (50-100 µM) ranges, the SDGs exhibited similar scavenging potentials; however at higher concentrations (250-500 µM), the inhibition by synthetic (S,S)-SDG-1 was significantly lower than those exerted by (R,R)-SDG-2 and natural (S,S)-SDG-1. Establishing regression lines for the potentials at low- and mid-concentration ranges (5-100 µM) allowed the free radical $EC_{50}$ scavenging activity of these compounds to be determined. As shown in FIG. 5, synthetic (R,R)-SDG-2 (123.63±8.67 µM) and synthetic (S,S)-SDG-1 (157.54±21.3 µM) were not significantly different. These values were similar to those exhibited by natural (S,S)-SDG-1 (83.94±2.80 µM) and α-tocopherol (132.81±12.57 µM) but considerably lower than that shown by ascorbic acid (439.56±11.81 µM).

These results are comparable to those reported for SDG (Moree, S.; Khanum, S. A.; Rajesha, J. *Free Rad. Antiox.* 2011, 1, 31).

It will be appreciated by those skilled in the art that changes could be made to the embodiments described above without departing from the broad inventive concept thereof. It is understood, therefore, that this invention is not limited to the particular embodiments disclosed, but it is intended to cover modifications that are within the spirit and scope of the invention, as defined by the appended claims.

What is claimed is:
1. A process for preparing a compound of formula ((S,S)-SDG-1)

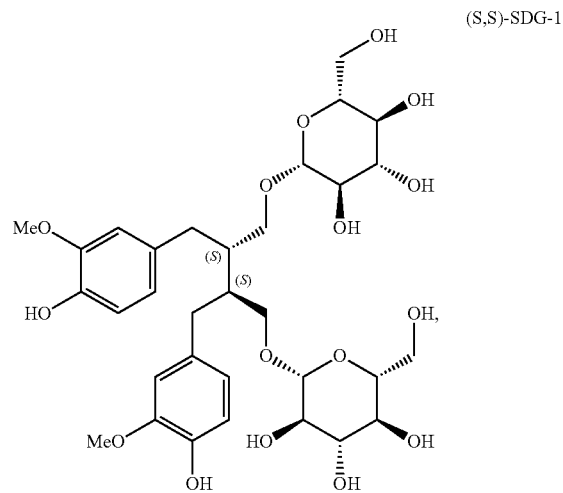

the process comprising:

(a) reacting a compound of formula (6)

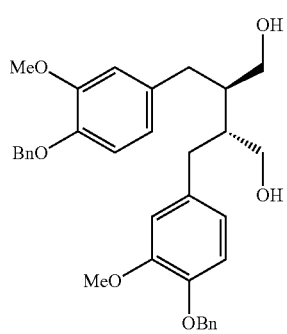

with a compound of formula (7)

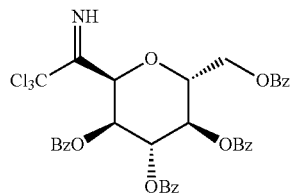

to prepare a compound of formula ((S,S)-S3)

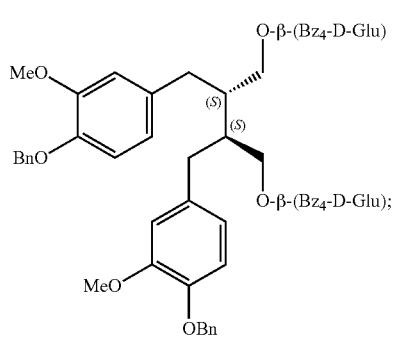

(b) cleaving benzyl ethers of the compound of formula ((S,S)-S3), followed by a separation procedure to prepare a compound of formula ((S,S)-8)

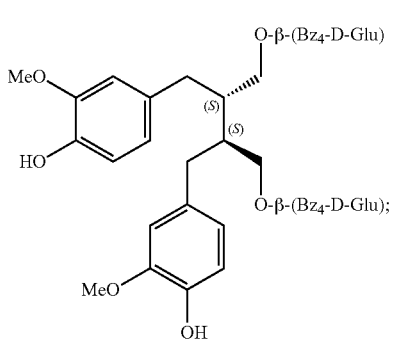

and
(c) deprotecting the compound of formula ((S,S)-8) to prepare the compound of formula ((S,S)-SDG-1).

2. The process of claim 1, wherein said reacting is carried out in the presence of a Lewis acid.

3. The process of claim 2, wherein said Lewis acid is TMSOTf.

4. The process of claim 3, wherein said reacting is carried out in the presence of activated molecular sieves.

5. The process of claim 1, wherein said cleaving is carried out in the presence of $H_2$ and Pd/C in MeOH.

6. The process of claim 1, wherein said separation procedure is carried out using preparative thin layer chromatography.

7. The process of claim 1, wherein said deprotecting is carried out in a solution of NaOMe and MeOH.

8. The process of claim 1, wherein said compound of formula (6) is prepared by the process comprising reacting a compound of formula (S2)

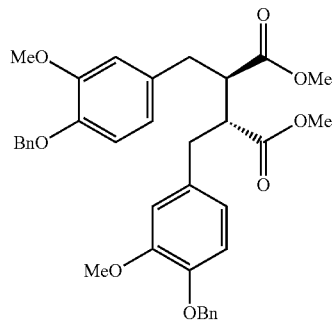

with a reducing agent to prepare the compound of formula (6).

9. The process of claim 8, wherein said reducing agent is lithium aluminum hydride (LAH) in THF.

10. The process of claim 8, wherein said compound of formula (S2) is prepared by the process comprising reacting a compound of formula (S1)

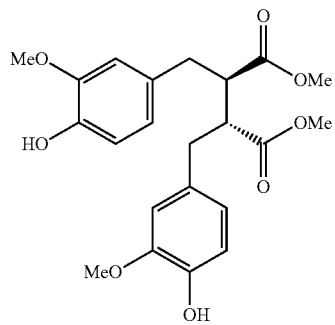

with a benzylating agent to prepare the compound of formula (S2).

11. The process of claim 10, wherein said benzylating agent is BnBr and NaH.

12. The process of claim 10, wherein said compound of formula (S1) is prepared by the process comprising reacting a compound of formula (5)

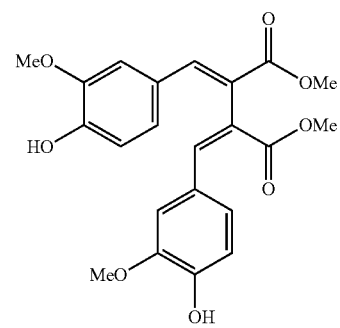

with a reducing agent to prepare the compound of formula (S1).

13. The process of claim 12, wherein said reducing agent is $H_2$ and Pd/C.

14. The process of claim 12, wherein said compound of formula (5) is prepared by the process comprising reacting a compound of formula (4)

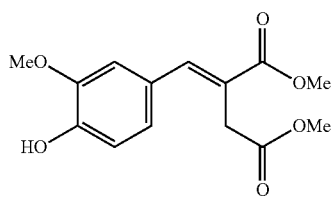

with vanillin by a Stobbe condensation reaction, followed by an esterification reaction to prepare the compound of formula (5).

15. The process of claim 14, wherein said Stobbe condensation reaction is carried out in MeOH and in the presence of lithium.

16. The process of claim 15, wherein said lithium is in the form of lithium wires.

17. The process of claim 14, wherein said compound of formula (4) is prepared by the process comprising reacting vanillin with methyl succinate via a Stobbe condensation reaction, followed by an esterification reaction.

18. The process of claim 17, wherein said Stobbe condensation reaction is carried out in MeOH and in the presence of lithium wires.

19. A process for preparing a compound of formula ((S,S)-SDG-1)

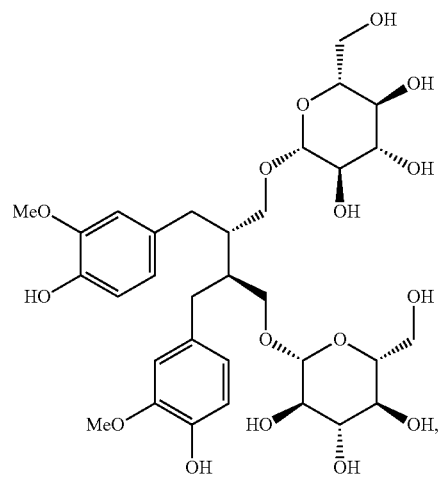

the process comprising:
(a) reacting a compound of formula (S2)

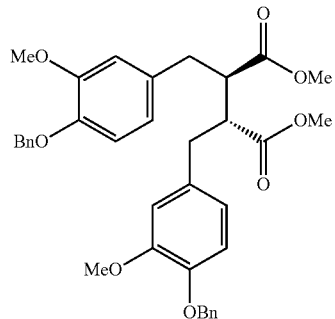

with a reducing agent to prepare a compound of formula (6)

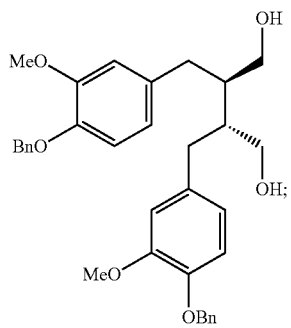

(b) reacting the compound of formula (6) with a compound of formula (7)

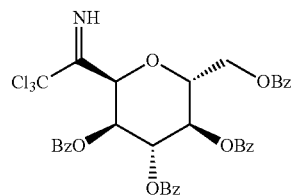

to prepare a compound of formula ((S,S)-S3)

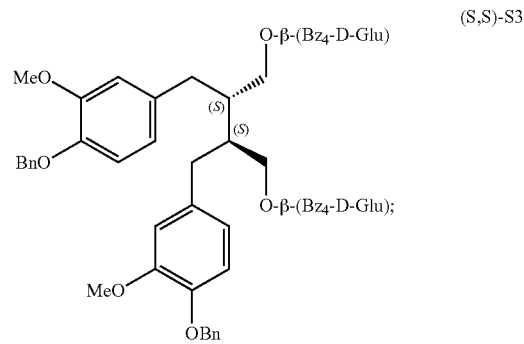

(c) cleaving benzyl ethers of the compound of formula ((S,S)-S3), followed by a separation procedure to prepare a compound of formula ((S,S)-8)

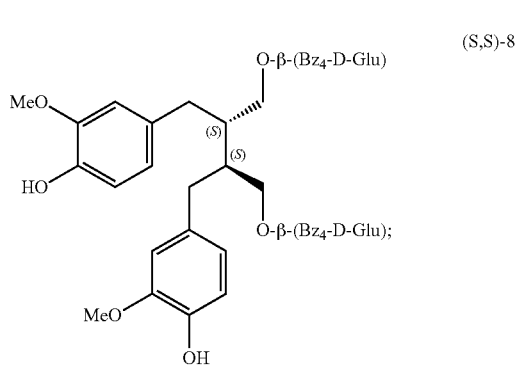

and (d) deprotecting the compound of formula ((S,S)-8) to prepare the compound of formula ((S,S)-SDG-1).

20. A process for preparing a compound of formula ((S,S)-SDG-1)

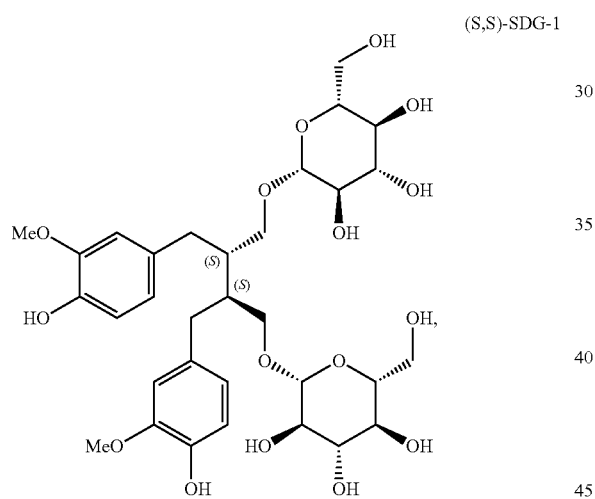

the process comprising:

(a) reacting a compound of formula (5)

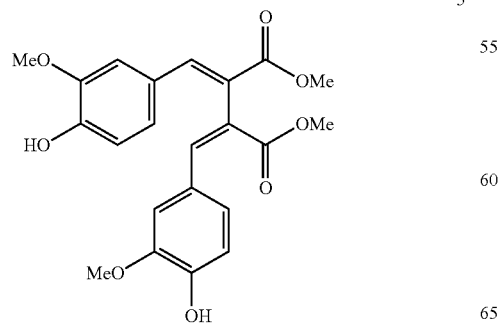

with a reducing agent to prepare a compound of formula (S1)

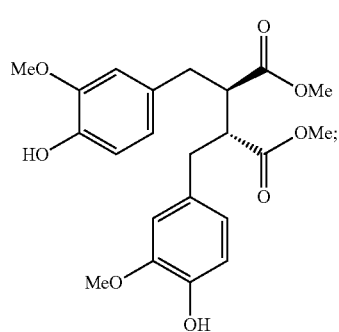

(b) reacting the compound of formula (S1)

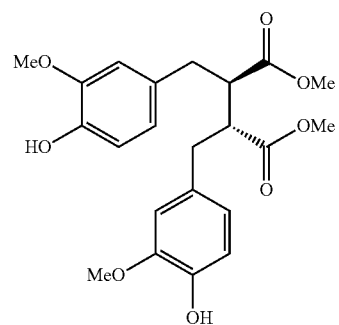

with a benzylating agent to prepare a compound of formula (S2)

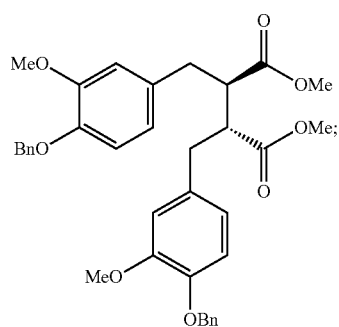

(c) reacting the compound of formula (S2) with a reducing agent to prepare a compound of formula (6)

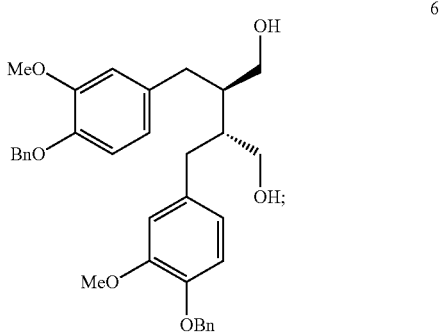 [SMILES: COc1cc(C[C@@H](CO)[C@H](CO)Cc2ccc(OCc3ccccc3)c(OC)c2)ccc1OCc1ccccc1]

(d) reacting the compound of formula (6) with a compound of formula (7)

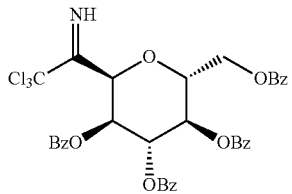

to prepare a compound of formula ((S,S)-S3)

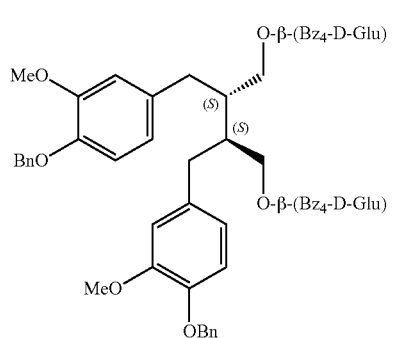

(e) cleaving benzyl ethers of the compound of formula ((S,S)-S3), followed by a separation procedure to prepare a compound of formula ((S,S)-8)

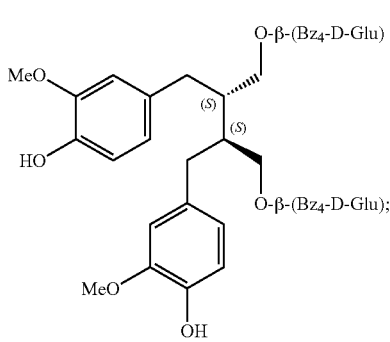

and
(f) deprotecting the compound of formula ((S,S)-8) to prepare the compound of formula ((S,S)-SDG-1).

21. A process for preparing a compound of formula ((R,R)-SDG-2)

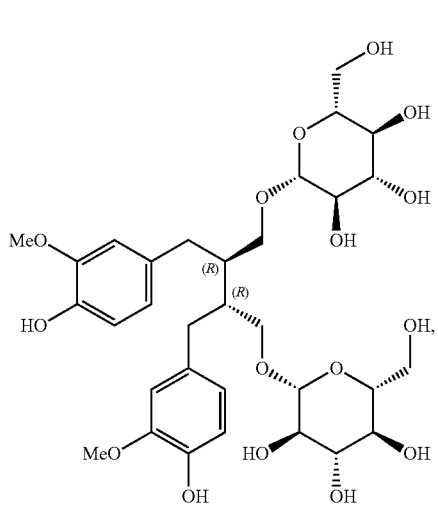

the process comprising:
(a) reacting a compound of formula (6)

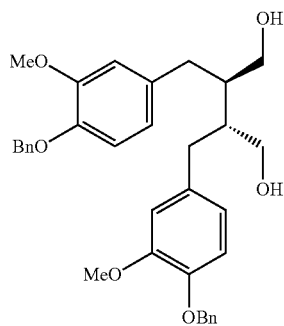

with a compound of formula (7)

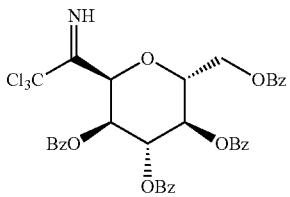

to prepare a compound of formula ((R,R)-S4)

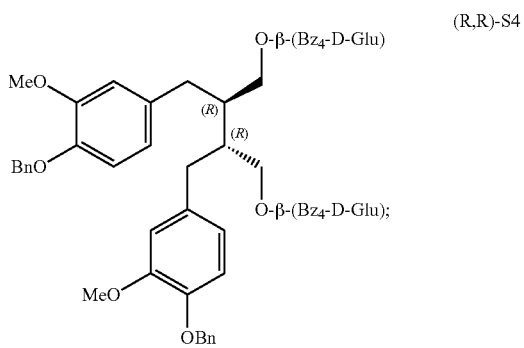

(b) cleaving benzyl ethers of the compound of formula ((R,R)-S4), followed by a separation procedure to prepare a compound of formula ((R,R)-9)

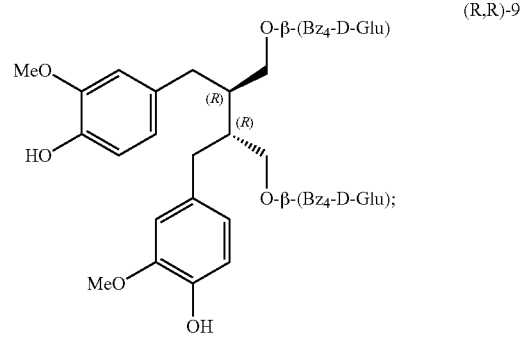

and
(c) deprotecting the compound of formula ((R,R)-9) to prepare the compound of formula ((R,R)-SDG-2).

22. The process of claim 21, wherein said reacting is carried out in the presence of TMSOTf.

23. The process of claim 21, wherein said reacting is carried out in the presence of activated molecular sieves.

24. The process of claim 21, wherein said cleaving is carried out in the presence of H₂ and Pd/C in MeOH.

25. The process of claim 21, wherein said separation procedure is carried out using preparative thin layer chromatography.

26. The process of claim 21, wherein said deprotecting is carried out in a solution of NaOMe and MeOH.

27. The process of claim 21, wherein said compound of formula (6) is prepared by the process comprising reacting a compound of formula (S2)

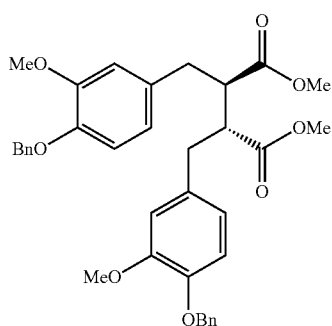

S2 with a reducing agent to prepare the compound of formula (6).

28. The process of claim 27, wherein said reducing agent is lithium aluminum hydride (LAH) in THF.

29. The process of claim 27, wherein said compound of formula (S2) is prepared by the process comprising reacting a compound of formula (S1)

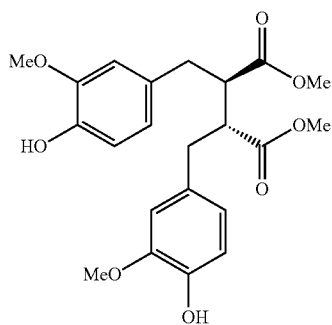

S1 with a benzylating agent to prepare the compound of formula (S2).

30. The process of claim 29, wherein said benzylating agent is BnBr and NaH.

31. The process of claim 29, wherein said compound of formula (S1) is prepared by the process comprising reacting a compound of formula (5)

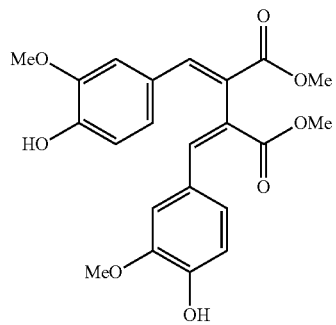

5 with a reducing agent to prepare the compound of formula (S1).

32. The process of claim 31, wherein said reducing agent is H₂ and Pd/C.

33. The process of claim 31, wherein said compound of formula (5) is prepared by the process comprising reacting a compound of formula (4)

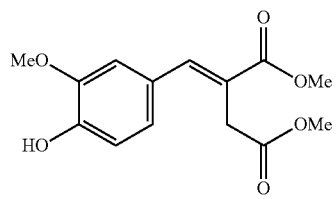

4 with vanillin by a Stobbe condensation reaction, followed by an esterification reaction to prepare the compound of formula (5).

34. The process of claim 33, wherein said Stobbe condensation reaction is carried out in MeOH and in the presence of lithium.

35. The process of claim 33, wherein said lithium is in the form of lithium wires.

36. The process of claim 33, wherein said compound of formula (4) is prepared by the process comprising reacting vanillin with methyl succinate via a Stobbe condensation reaction, followed by an esterification reaction.

37. The process of claim 36, wherein said Stobbe condensation reaction is carried out in MeOH and in the presence of lithium wires.

38. A process for preparing a compound of formula ((R,R)-SDG-2)

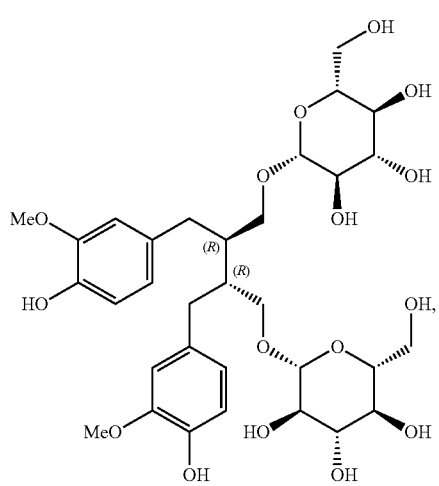

(R,R)-SDG-2 the process comprising:
(a) reacting a compound of formula (S2)

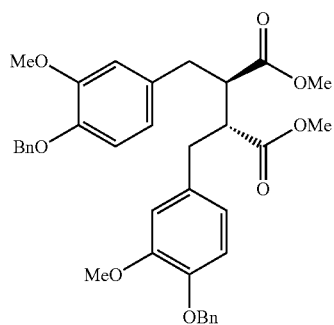

S2 with a reducing agent to prepare a compound of formula (6)

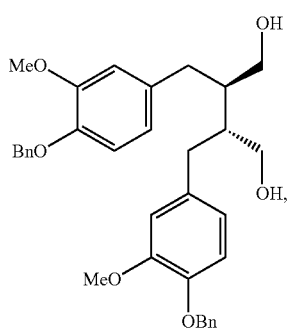

6

(b) reacting the compound of formula (6) with a compound of formula (7)

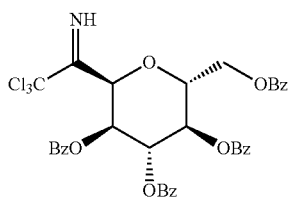

7 to prepare a compound of formula ((R,R)-S4)

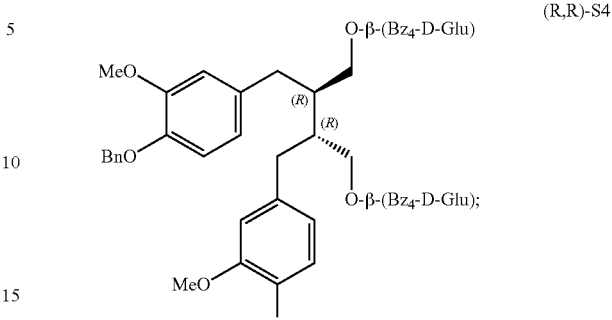

(R,R)-S4

(c) cleaving benzyl ethers of the compound of formula ((R,R)-S4), followed by a separation procedure to prepare a compound of formula ((R,R)-9)

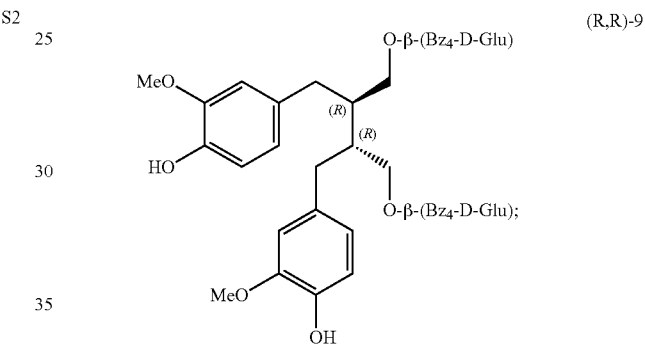

(R,R)-9 and (d) deprotecting the compound of formula ((R,R)-9) to prepare the compound of formula ((R,R)-SDG-2).

39. A process for preparing a compound of formula ((R,R)-SDG-2)

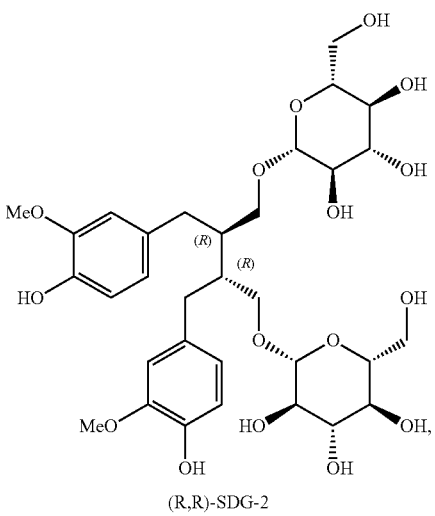

(R,R)-SDG-2 the process comprising:
(a) reacting a compound of formula (5)

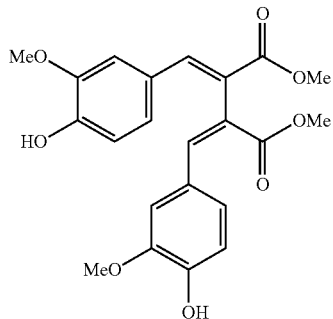

5 with a reducing agent to prepare a compound of formula (S1)

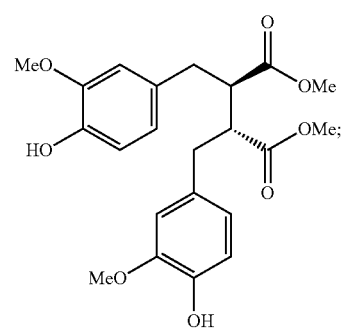

S1

(b) reacting the compound of formula (S1)

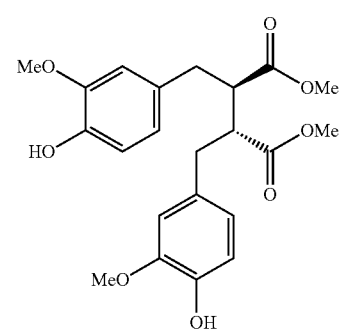

S1 with a benzylating agent to prepare a compound of formula (S2)

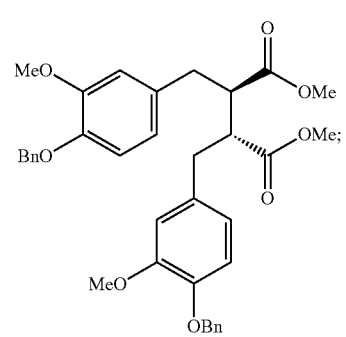

S2

(c) reacting the compound of formula (S2) with a reducing agent to prepare a compound of formula (6)

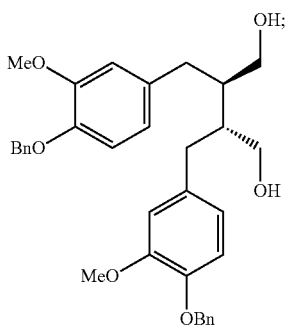

6

(d) reacting the compound of formula (6) with a compound of formula (7)

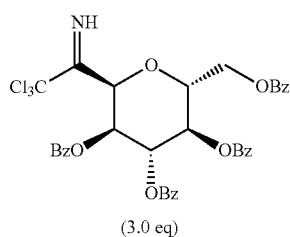

7

(3.0 eq)

to prepare a compound of formula ((R,R)-S4)

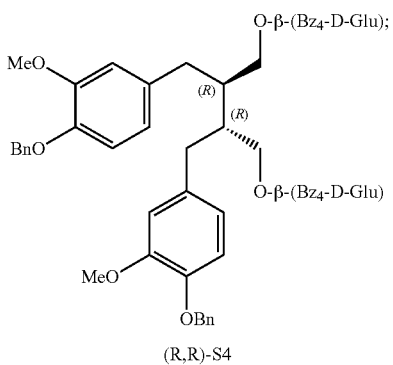

(R,R)-S4

(e) cleaving benzyl ethers of the compound of formula ((R,R)-S3), followed by a separation procedure to prepare a compound of formula ((R,R)-9)
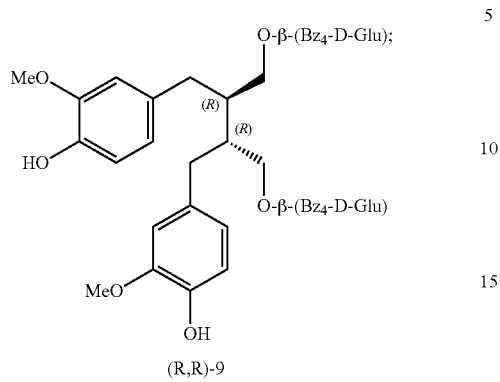
(R,R)-9
and
(f) deprotecting the compound of formula ((R,R)-9) to prepare the compound of formula ((R,R)-SDG-2).
* * * * *

UNITED STATES PATENT AND TRADEMARK OFFICE
CERTIFICATE OF CORRECTION

PATENT NO.         : 10,030,040 B2
APPLICATION NO.    : 14/897181
DATED              : July 24, 2018
INVENTOR(S)        : Melpo Christofidou-Solomidou et al.

Page 1 of 1

It is certified that error appears in the above-identified patent and that said Letters Patent is hereby corrected as shown below:

In the Specification

Please replace Lines 22-25 in Column 1 with the following:
This invention was made with government support under grant numbers CA133470 and AI081251 awarded by the National Institutes of Health. The government has certain rights in the invention.

Signed and Sealed this
Nineteenth Day of February, 2019

Andrei Iancu
*Director of the United States Patent and Trademark Office*